(12) United States Patent
Zheng et al.

(10) Patent No.: US 8,383,818 B2
(45) Date of Patent: Feb. 26, 2013

(54) FUNCTIONALLY SELECTIVE ALPHA2C ADRENORECEPTOR AGONISTS

(75) Inventors: Junying Zheng, New Providence, NJ (US); Jianhua Chao, Pompton Lakes, NJ (US); Kevin D. McCormick, Basking Ridge, NJ (US); Robert G. Aslanian, Rockaway, NJ (US); Mwangi W. Mutahi, Nyeri (KE); Christopher W. Boyce, Flemington, NJ (US); Walter S. Won, Alpine, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 148 days.

(21) Appl. No.: 12/918,427

(22) PCT Filed: Feb. 19, 2009

(86) PCT No.: PCT/US2009/034454
§ 371 (c)(1),
(2), (4) Date: Nov. 22, 2010

(87) PCT Pub. No.: WO2009/105504
PCT Pub. Date: Aug. 27, 2009

(65) Prior Publication Data
US 2011/0060006 A1    Mar. 10, 2011

Related U.S. Application Data

(60) Provisional application No. 61/030,340, filed on Feb. 21, 2008.

(51) Int. Cl.
*C07D 215/04*    (2006.01)
(52) U.S. Cl. .................................................... 546/152
(58) Field of Classification Search .................. None
See application file for complete search history.

(56) References Cited

U.S. PATENT DOCUMENTS

2006/0069143 A1 *  3/2006  Heidelbaugh et al. ........ 514/389
2008/0027100 A1     1/2008  McCormick et al.

OTHER PUBLICATIONS

Pindur, U. et al. New Reactions of Vinylindoles as Heterocyclic Dienes with 4-phenyl-1,2,4-triazoline-3,5-dione: Non-Concerted versus Concerted Processes. Chimia. 1990, vol. 44, p. 340, scheme 3, compound 10.*
Pindur et al., "New Reactions of Vinylindoles as Heterocylic Dienes with 4-Phyenyl-1,2,4-Triazoline-3,5-Dione, Non-Concerted Versus Concerted Processes", 1990, vol. 44, No. 10, pp. 339-341, Chimia.
Hubert et al., "Heterocyclic Steroids. XIV. Total Synthesis of d1-8,9-Dehydro-13-Azaestrone Methyl Ether", Tetrahedron Letters, vol. 20, pp. 1553-1556, 196.
Fan et al., Database Chemical Abstract "Crystal Structures of 1,2-Dimethyl-3-Indolymethylidenesuccinic Fulgide Anhydride and 1,2-Dimethyl-3-Indolylethylidenesuccinic Fulgide Anhydride", XP002540398, 1993:223190.

* cited by examiner

*Primary Examiner* — Rebecca Anderson
*Assistant Examiner* — Ana Muresan
(74) *Attorney, Agent, or Firm* — H. Eric Fischer; Gerard M. Devlin

(57) ABSTRACT

In its many embodiments, the present invention provides a novel class of heterocyclic derivatives as a2C adrenergic receptor agonists, methods of preparing such compounds, pharmaceutical compositions containing one or more such compounds, methods of preparing pharmceutical formulations comprising one or more such compounds, and methods of treatment, prevention, inhibition, or amelioration of one or more conditions associated with the a2C adrenergic receptors using such compounds or pharmaceutical compositions.

4 Claims, No Drawings

FUNCTIONALLY SELECTIVE ALPHA2C ADRENORECEPTOR AGONISTS

RELATED APPLICATIONS

This application claims benefit to U.S. Provisional application Ser. No. 61/030,340, filed Feb. 21, 2008, herein incorporated by reference.

FIELD OF THE INVENTION

The present invention relates to compounds useful as α2C adrenergic receptor agonists, methods for making the compounds, pharmaceutical compositions containing the compounds, and methods of treatment and prevention using the compounds and compositions to treat disease states such as congestion (including nasal), migraine, congestive heart failure, cardiac ischemia, glaucoma, stress-induced urinary incontinence, attention deficit hyperactivity disorder, pain and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist RP, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into α1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $α_1$-Adrenoceptor Subtypes," Naunyn-Schmiedeberg's Arch. Pharmacol, 352:1-10 (1995); Macdonald et al., "Gene Targeting-Homing in on $α_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art and are described in numerous patents and scientific publications. It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders (e.g., schizophrenia).

For example, published PCT application WO 02/076950 discloses compounds having α2 agonist activity of the following general formula:

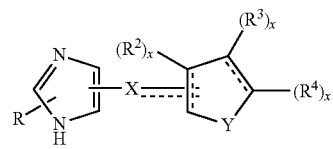

Other publications disclosing similar compounds includes WO 01/00586, WO 99/28300, U.S. Pat. No. 6,841,684 B2 and US 2003/0023098 A1.

Another class of compounds having α2-agonist properties is disclosed in U.S. Pat. No. 5,658,938, and has the following general formula:

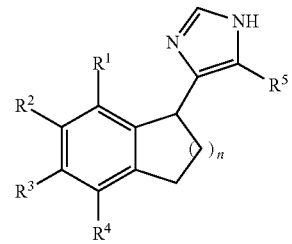

wherein n=1-2, $R^1$-$R^3$ represent hydrogen, halogen hydroxy, alkyl or alkoxy, and $R^5$ is hydrogen or alkyl.

Another class of compounds reported to have affinity for α2 receptors includes the following two compounds (Bagley et. al., J. Med. Chem. Res. 1994, 4:346-364):

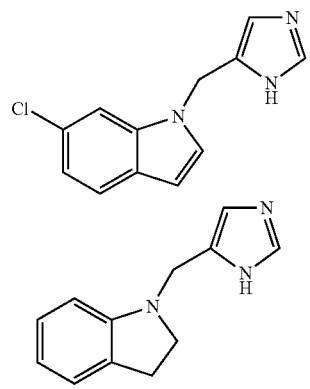

It is also known that compounds having adrenergic activity, such as α2A agonists, may be associated with undesirable side effects. Examples of such side effects include hyper- and hypotension, sedation, locomotor activity, psychotic disorders (e.g., schizophrenia).

Another class of compounds reported to have affinity for α2 receptors includes the following two compounds (Miller et. al., *J. Med. Chem.* 1994, 37:2328-2333; *J. Med. Chem.* 1996, 39:3001-3013; *J. Med. Chem.* 1997, 37:3014-3024):

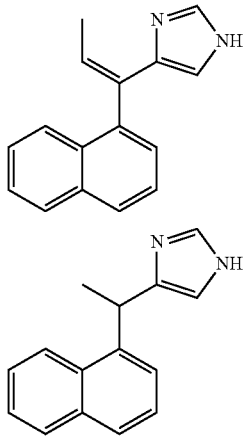

Another class of indane and tetrahyrdonaphthalene type compounds having α2-agonist properties is disclosed in PCT application WO 97/12874 and WO20040506356. This class has the following general formula:

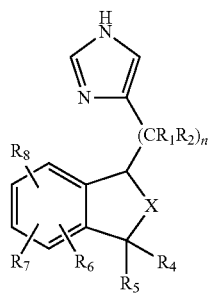

wherein n=0-1, X is 1 or 2 carbon units, $R_4$ is H, OH, alkyl, or alkoxy, $R_5$ may be taken together with $R^4$ to form a carbonyl, and $R^6$-$R^8$=H, OH, SH, alkyl, alkenyl, cycloalkyl, alkoxy, hydroxyalkyl, alkylthio, alkylthiol, halo, $CF_3$, $NO_2$, or alkylamino. This class specifically includes MPV-2426 (fadolmidine) and its prodrug esters:

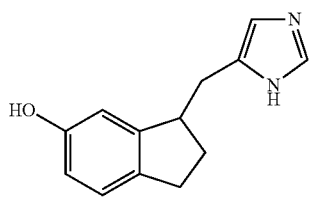

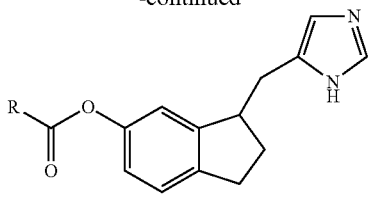

wherein R is optionally substituted lower alkyl, aryl, cycloalkyl, heteroaryl, lower alkylamino, and saturated 5- or 6-membered heterocyclic groups containing 1 or 2 N atoms.

Further, other classes of compounds that exhibit functional selectivity for the alpha 2C receptor have been discovered. Application U.S. Ser. No. 11/508,458, filed Aug. 23, 2006, discloses indoline compounds that possess this activity and application U.S. Ser. No. 11/508,467, filed on the same date, describes morpholine compounds that are functionally selective of the alpha 2C receptor. CIP applications of these applications have been filed; the Ser. Nos. are 11/705,673 and 11/705,683, both filed on Feb. 13, 2009.

Additional applications which have been filed that disclose alpha2C receptor agonists are application WO 2008/100,456 which claims benefit to provisional application U.S. Ser. No. 60/901,045, application WO 2008/100,459, which claims benefit to provisional applications U.S. Ser. No. 60/901,071 and 60/972,892 and application WO 2008/100,480, which claims benefit to provisional application U.S. Ser. No. 60/901,064.

It is also known that compounds having adrenergic activity, such as α2A agonists, may be associated with undesirable side effects. Examples of such side effects include hyper- and hypotension, sedation, locomotor activity, and body temperature variations.

Moreover, substituted indolinone-type compounds are known in the art for treating cancer. Such compounds are described in US 2005/0090541 A1 (Berlex Biosciences) and WO 2007/008664 A1 (Allergan).

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype and that act functionally selectively as agonists of the α2C or the α2B/2C receptor subtype in preference over the α2A receptor subtype possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is ≧30% $E_{max}$ (GTPγS assay) and its efficacy at the α2A receptor is ≦30% $E_{max}$, (GTPγS assay).

There is a need for new compounds, formulations, treatments and therapies to treat diseases and disorders associated with α2C adrenergic receptors while minimizing adverse side effects. Further, there is a need to develop compounds that are functionally selective for the α2C or the α2B/2C receptor subtype with respect to the α2A receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds that are functionally selective α2C adrenergic receptor agonists, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts or metabolites, solvates, prodrugs or polymorphs of said compound, said compound having the general structure shown in Formula I

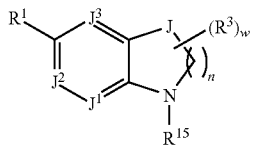

wherein:
J is:

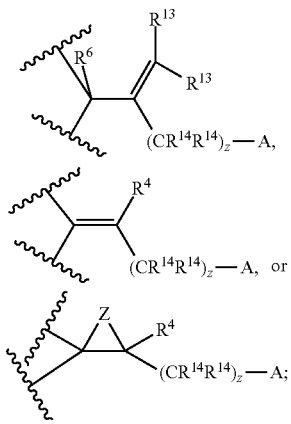

$J^1$, $J^2$ and $J^3$ are independently —N—, —N(O)—, or —C($R^2$—;

Z is —[C($R^c$)($R^c$)]$_x$—;

A is a 5-membered heteroaryl, heterocyclyl or heterocyclenyl ring containing 1-3 heteroatoms, preferably selected from the group consisting of —O—, —S— and —N—, and is optionally substituted with at least one (preferably 1 to 5, more preferably 1 to 3) $R^5$ and/or 1 or 2 (=O) (carbonyl) groups;

$R^1$ is selected from the group consisting of H, —CN, —[C($R^a$)($R^b$)]$_q$YR$^{7'}$, —[C($R^a$)($R^b$)]$_q$N($R^7$)YR$^{7'}$, —[C($R^a$)($R^b$)]$_q$NR$^7$R$^{7'}$, —[C($R^a$)($R^b$)]$_q$OYR$^{7'}$, —[C($R^a$)($R^b$)]$_q$N(YR$^{7'}$)(YR$^{7'}$), and —[C($R^a$)($R^b$)]$_q$ON═CR$^7$R$^{7'}$;

Y is selected from the group consisting of a bond, —C(═O)—, —C(═O)NR$^7$—, —C(═O)O—, —C(═O)—[C($R^a$)($R^b$)]$_n$—O—C(═O)—, —C(═O)N($R^c$)—O—, —C(═NR$^7$)—, —C(═NOR$^7$)—, —C(═NR$^7$)NR$^7$—, —C(═NR$^7$)NR$^7$O—, —C(═N—CN)—, —S(O)$_p$—, —SO$_2$NR$^7$—, and —C(═S)NR$^7$—;

wherein $R^a$ and $R^b$ are independently selected from the group consisting of H, alkyl, alkoxy, and halo, and $R^c$ is H or alkyl;

$R^2$ is independently selected from the group consisting of H, —OH, halo, —CN, —NO$_2$, —S(O)$_p$R$^7$, —NR$^7$R$^{7'}$, —[C($R^a$)($R^b$)]$_q$YR$^{7'}$, —[C($R^a$)($R^b$)]$_q$N(R$^7$)YR$^{7'}$, —[C($R^a$)($R^b$)]═$_q$OYR$^{7'}$, and —(CH$_2$)$_q$ON═CR$^7$R$^{7'}$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^3$ is independently selected from the group consisting of H, halo, and (═O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$, provided that when w is 3, no more than 2 of the $R^3$ groups may be (═O);

$R^4$ is independently selected from the group consisting of H, —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (═O);

$R^6$ is independently selected from the group consisting of H —CN, and halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one (preferably 1 to 5, more preferably 1 to 3) of halo, —OH, —CN, —NO$_2$, —NR$^7$R$^{7'}$, and —S(O)$_p$R$^7$ substituents and/or 1 or 2 (═O), and —C(═O)R$^7$, —C(═O)OR$^7$, —C(═O)NR$^7$R$^{7'}$, —SO$_2$R$^7$ and —SO$_2$NR$^7$R$^{7'}$;

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetroclenyl, hetrocyclenylalkyl, heteroaryl, and heteroarylalkyl groups, each of which is optionally substituted one or more times (preferably 1 to 5, more preferably 1 to 3) by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetroclenyl, hetrocyclenylalkyl, heteroaryl, and heteroarylalkyl groups, each of which is optionally substituted one or more times (preferably 1 to 5, more preferably 1 to 3) by $R^{12}$; or a) when a variable is —NR$^7$R$^{7'}$, —C[($R^a$)($R^b$)]$_q$YR$^{7'}$, —C[($R^a$)($R^b$)]$_q$NR$^7$R$^{7'}$, —[C($R^a$)($R^b$)]$_q$OYR$^{7'}$, —(CH$_2$)$_q$NR$^7$R$^{7'}$, —C(O)NR$^7$R$^{7'}$, or —SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N($R^9$)— and S, wherein said rings are optionally substituted by 1 to 5 independently selected $R^5$ moieties and/or 1 or 2 (═O), or b) when a variable is —(CH$_2$)$_q$ON═CR$^7$R$^{7'}$ or —[C($R^a$)($R^b$)]$_q$ON═CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N($R^9$)— and S, wherein said rings are optionally substituted by 1 to 5 independently selected $R^5$ moieties and/or 1 or 2 (=O);

$R^9$ is independently selected from the group consisting of H, —C(O)—$R^{10}$, —C(O)—$OR^{10}$, and —S(O)$_p$—$OR^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N($R^{11}$)$_2$, and —S(O)$_p$$R^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) of halo, —OH, —CN, —NO$_2$, —N($R^{11}$)$_2$, and —S(O)$_p$$R^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one (preferably 1 to 5, more preferably 1 to 3) substituent independently selected from the group consisting of halo, —OH, —CN, —NO$_2$, —N($R^{11}$)$_2$, and —S(O)$_p$$R^{11}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N($R^{11}$)$_2$, and —S(O)$_p$$R^{11}$, and/or 1 or 2 (=O), and alkyl, alkoxy, alkenyl, alkenyloxy, alkynyl, cycloalkyl, cycloalkenyl, cycloalkoxy, aryl, aryl*, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least once (preferably 1 to 5, more preferably 1 to 3) by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N($R^{11}$)$_2$, and —S(O)$_p$$R^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more (preferably 1 to 5, more preferably 1 to 3) times by $R^{11}$;

$R^{13}$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one (preferably 1 to 5, more preferably 1 to 3) $R^5$;

$R^{14}$ is independently selected from the group consisting of H, alkyl, halo, —CN, and alkoxy;

$R^{15}$ is selected from the group consisting of H, —C(O)—$R^{10}$, and —S(O)$_p$$OR^{10}$ and alkyl, alkenyl, alkynyl, cycloalkyl, aryl, arylalkyl, heteroaryl, and heteroarylalkyl groups, each of which is optionally substituted with at least one (preferably 1 to 5, more preferably 1 to 3) halo, —OH, —CN, —NO$_2$, —N($R^{11}$)$_2$, and —S(O)$_p$$R^{11}$ and/or 1 or 2 (=O);

n is 1, 2 or 3;
w is 0, 1, 2, 3, or 4;
p is independently 0, 1 or 2;
q is independently an integer from 0-10;
z is 0, 1, 2, 3, 4, or 5; and
x is 1, 2, or 3
provided that when n is 1, then $R^3$ cannot be a carbonyl (=O) group.

The compounds of Formula I can be useful as α2C adrenergic receptor agonists, and can be useful in the treatment and prevention of allergic rhinitis, congestion (including, but not limited to nasal congestion), migraine, congestive heart failure, chronic heart failure, cardiac ischemia, glaucoma, stress-induced urinary incontinence, attention deficit hyperactivity disorder, neuronal damage from ischemia and psychotic disorders. Further, the compounds of Formula I can be useful in the treatment of pain (both chronic and acute), such as pain that is caused by inflammation, neuropathy, arthritis (including osteo and rheumatoid arthritis), diabetes (e.g., diabetes mellitus or diabetes insipidus) or pain of an unknown origin. Examples of neuropathic pain may include but not limited to; diabetic neuropathy, neuralgia of any etiology (e.g. post-herpetic, trigeminal), chemotherapy-induced neuropathy, HIV, lower back pain of neuropathic origin (e.g. sciatica), traumatic peripheral nerve injury of any etiology, central pain (e.g. post-stroke, thalamic, spinal nerve injury). Other pain that can be treated is nociceptive pain and pain that is visceral in origin or pain that is secondary to inflammation or nerve damage in other diseases or diseases of unknown origin. Further, these compounds can be useful in the treatment of symptoms of diabetes. Examples of symptoms of diabetes may include but are not limited to: hyperglycemia, hypertriglyceridemia, increased levels of blood insulin and hyperlipidemia.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to a mammal an effective dose of at least one compound having adrenergic activity wherein said compound is a functionally selective agonist of the α2C receptor, wherein the selective agonist of the α2c receptor has an efficacy that is greater than or equal to 30% $E_{max}$ when assayed in the GTPγS assay and its efficacy at the α2A receptor is ≤30% $E_{max}$ (GTPγS assay).

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In another embodiment, $J^1$, $J^2$ and $J^3$ are each —C($R^2$)—.
In another embodiment, $J^1$, $J^2$ and $J^3$ are each —CH—.
In another embodiment, A is unsubstituted imidazole.
In another embodiment, n is 1.

In another embodiment, n is 2.

In another embodiment, n is 3.

In another embodiment, p is an integer from 0-2.

In another embodiment, q is an integer 0-3.

In another embodiment, the present invention discloses compounds which are represented by structural formulae II, III, or IV or a pharmaceutically acceptable salt, solvate or ester thereof, Formula II Formula III Formula IV wherein the individual variables are defined above.

An embodiment of compounds of formulae II are those wherein:

A is $R^1$ is —[C($R^a$)($R^b$)]$_q$N($R^7$)Y$R^{7'}$

Y is —C(=O)—, —C(=O)O— or —C(=O)N$R^7$;

z' is 1 or 2; and n is 2.

Another embodiment of compounds of formula II is those compounds of the formula:

Formula IIa or a pharmaceutically acceptable salt, solvate or ester thereof wherein n is 2 or 3;

$J^1$ is CH;

$J^2$ is CH;

$J^3$ is CH;

$R^1$ is —[C($R^a$)($R^b$)]$_q$N($R^7$)Y$R^{7'}$

Y is —C(=O)—, —C(=O)O— or —C(=O)N$R^7$ z' is 1 or 2;

$R^4$ is H;

$R^5$ is H;

$R^7$ is independently H, alkyl, cycloalkyl, or arylalkyl;

$R^{7'}$ is H or alkyl; and w is 0.

Another embodiment of compounds of formula III is those compounds of the formula:

Formula IIIa or a pharmaceutically acceptable salt, solvate or ester thereof wherein z' is 1 or 2; and $R^{13}$ is H in both occurrences.

Compounds falling within Formula I are those shown below:

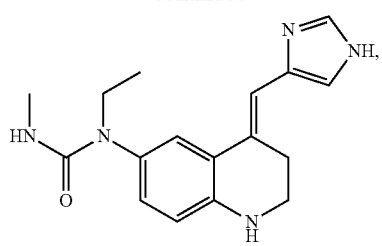
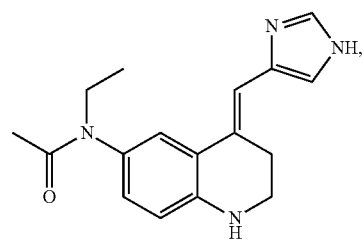
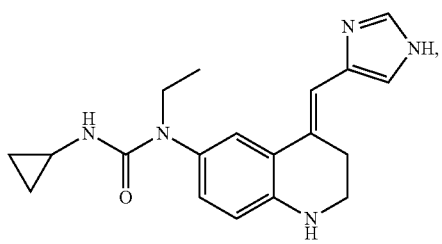
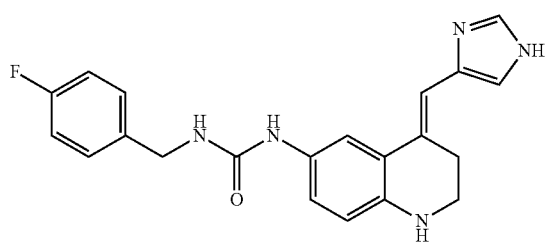
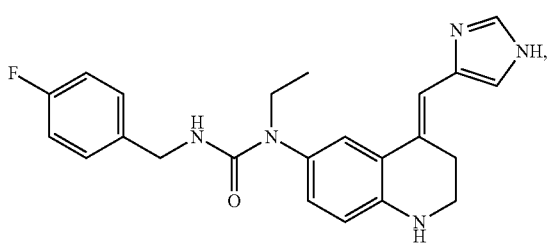
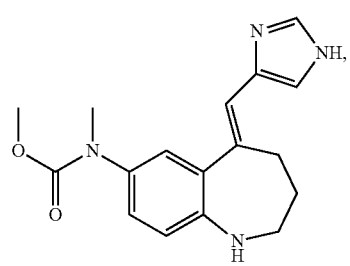
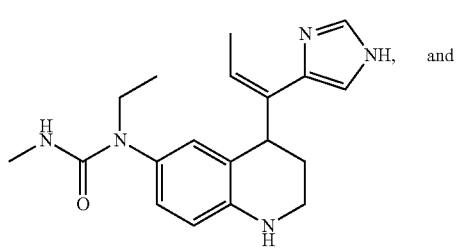
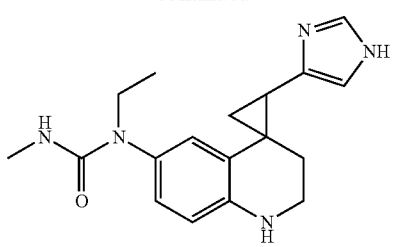
as well as the pharmaceutically acceptable prodrugs, salts, solvates or esters of each of these compounds.
Another group of compounds falling within Formula I are those shown below:
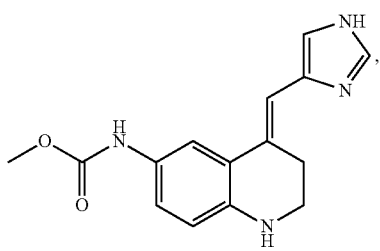
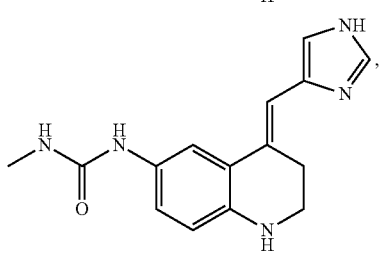
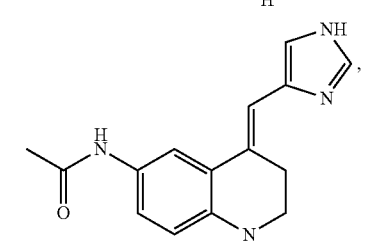
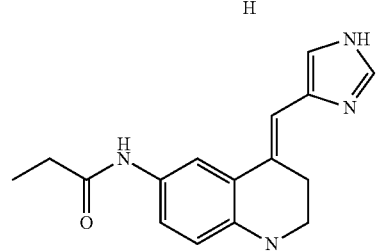
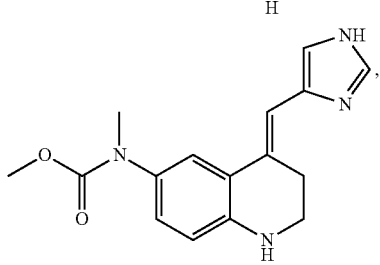

-continued

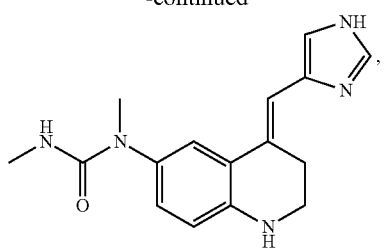

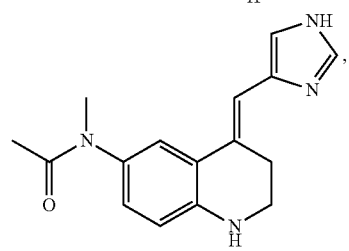

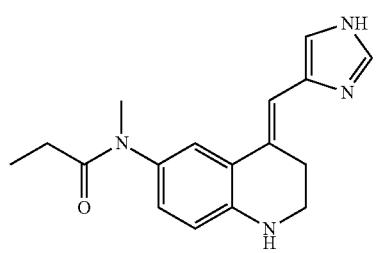

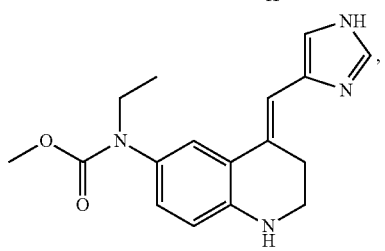

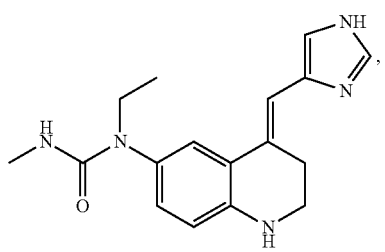

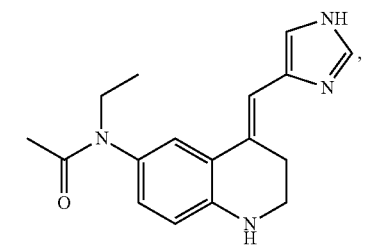

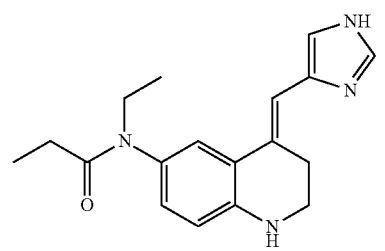

-continued

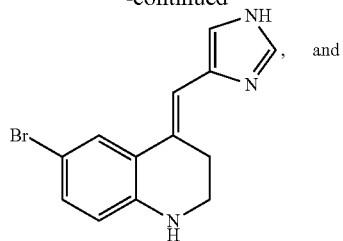

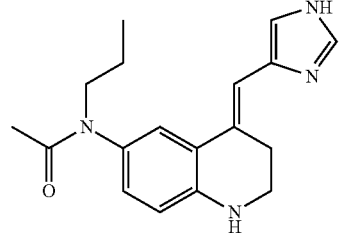

as well as the pharmaceutically acceptable prodrugs, salts, solvates or esters of each of these compounds.

A preferred group of compounds are:

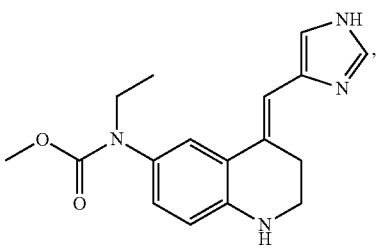

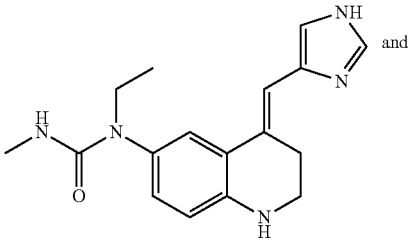

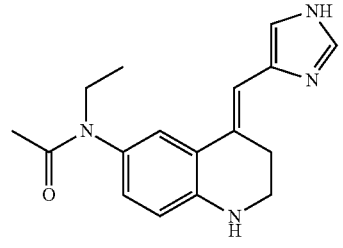

as well as the pharmaceutically acceptable prodrugs, salts, solvates or esters of each of these compounds.

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system, in which at least one of the multicyclic rings is an aryl ring, comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. Non-limiting examples of aryl multicyclic ring systems include:

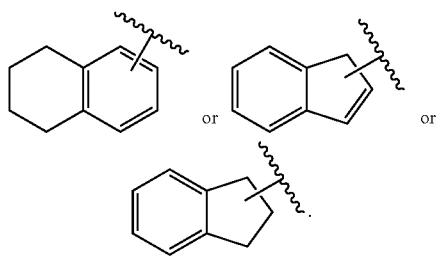

"Heteroaryl" means an aromatic monocyclic or multicyclic ring system, in which at least one of the multicyclic rings is aromatic, comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

Non-limiting examples of hetreroaryl multicyclic ring systems include:

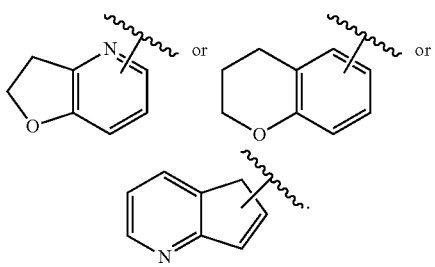

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, imidazolidinyl, pyrazolidinyl, piperazinyl, morpholinyl, thiomorpholinyl, thiazolidinyl, 1,4-dioxanyl, tetrahydrofuranyl, tetrahydrothiophenyl, and the like.

Compounds of Formula I and salts, esters, solvates and prodrugs thereof, may exist in their tautomeric form (for example, as an amide or imino ether). All such tautomeric forms are contemplated herein as part of the present invention. Non-limiting examples of tautomeric forms that are part of this invention are as follows:

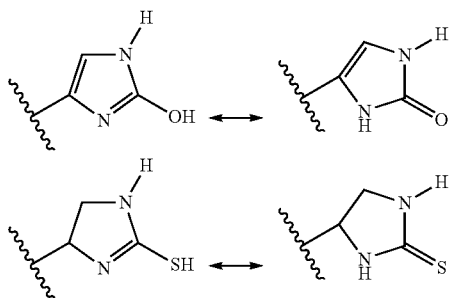

It should be noted that in saturated heterocyclyl containing systems of this invention, there are no hydroxyl, amino, or thiol groups on carbon atoms adjacent to a N, O or S atom. Thus, for example, in the ring:

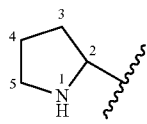

there is no —OH attached directly to carbons marked 2 and 5. It should also be noted that this definition does not preclude (=O), (=S), or (=N) substitutions, or their tautomeric forms, on C atoms adjacent to a N, O or S. Thus, for example, in the above ring, (=O) substitution on carbon 5, or its imino ether tautomer is allowed.

Non-limiting examples which illustrate the present invention are as follows:

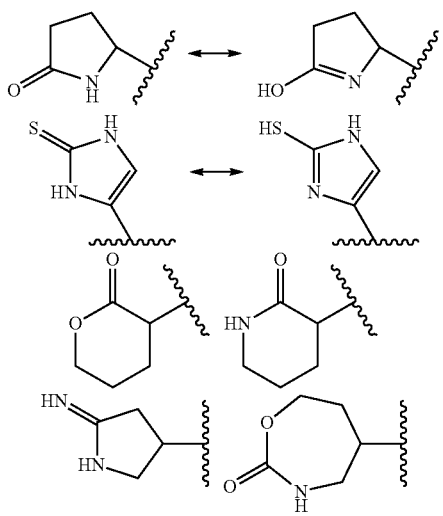

The following non-limiting examples serve to illustrate radicals not contemplated by the present invention:

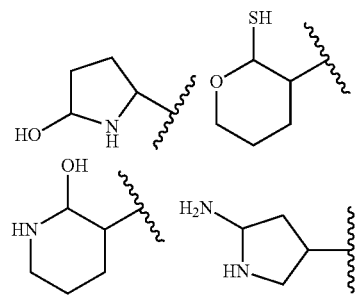

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinyipropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, 2-oxazolinyl, 2-thiazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclenylalkyl" means a heterocyclenyl-alkyl group in which the heterocyclenyl and the alkyl are as previously described.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C (O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" or "arylalkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Heteroarylalkoxy" means a heteroarylalkyl-O-group in which the heteroarylalkyl group is as previously described.

"Heterocyclylalkoxy" means a heterocyclylalkyl-O group in which the hetrocyclylalkyl group is as previously described.

"Heterocyclenylalkoxy" means a heterocyclenylalkyl-O group in which the heterocyclenylalkyl group is as previously described.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those, in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

It is noted that carbons of Formula I can be replaced with 1-3 silicon atoms, provided all valency requirements are satisfied.

The term "optionally substituted" means optional substitution with the specified groups, radicals or moieties.

The straight line ——— as a bond generally indicates a mixture of, or either of, the possible isomers, non-limiting example(s) include, containing (R)— and (S)— stereochemistry. For example,

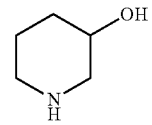

means containing both

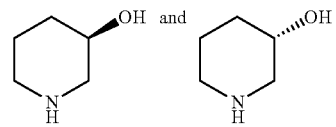 [SMILES: O[C@@H]1CCCNC1 ; "and" ; O[C@H]1CCCNC1]

A dashed line (-----) represents an optional bond.
Lines drawn into the ring systems, such as, for example:

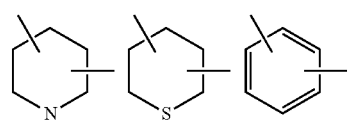

indicate that the indicated line (bond) may be attached to any of the substitutable ring atoms, non-limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

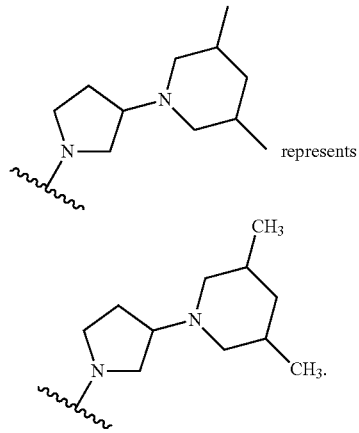

represents

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or formula, its definition on each occurrence is independent of its definition at every other occurrence.

Unless defined otherwise, all definitions for the variables follow the convention that the group to the right forms the point of attachement to the molecule; i.e., if a definition is arylalkyl, this means that the alkyl portion of the definition is attached to the molecule.

Further, all divalent variable are attached from left to right. For example when $R^1$ is —$[C(R^a)(R^b)]_qN(R^7)Y_1R^{7'}$ and Y is —C(=O)—, —C(=O)O— or —C(=O)NR$^7$, then $R^1$ forms the group —$[C(R^a)(R^b)]_qN(R^7)$—C(=O)—$R^{7'}$, —$[C(R^a)(R^b)]_qN(R^7)$—C(=O)O—$R^{7'}$, or —$[C(R^a)(R^b)]_qN(R^7)$—C(=O)N(R^7)(R^{7'})$.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as ($\beta$-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, $\alpha$-amino ($C_1$-$C_4$)alkanyl, arylacyl and $\alpha$-aminoacyl, or $\alpha$-aminoacyl-$\alpha$-aminoacyl, where each $\alpha$-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural $\alpha$-aminoacyl or natural $\alpha$-aminoacyl, —C(OH)C(O)OY$^1$ wherein Y' is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al,

*AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Metabolic conjugates, such as glucuronides and sulfates which can undergo reversible conversion to the compounds of Formula I are contemplated in the present invention.

"Effective amount" or "therapeutically effective amount" is meant to describe an amount of compound or a composition of the present invention effective in producing the desired therapeutic, ameliorative, inhibitory or preventative effect.

The terms "purified", "in purified form" or "in isolated and purified form," as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula I or may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula I incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formulae Ia or Ib may be atropisomers (e.g., substituted biaryls) and are considered as part of this invention. Enantiomers can also be separated by use of chiral HPLC column.

Polymorphic forms of the compounds of Formula I, and of the salts, solvates and prodrugs of the compounds of Formula I, are intended to be included in the present invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more therapeutic agents such as, for example, glucocorticosteroids, PDE-4 inhibitors, anti-muscarinic agents, cromolyn sodium, H₁ receptor antagonists, 5-HT₁ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma.

Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, and cortisone.

Suitable PDE-4 inhibitors include roflumilast, theophylline, rolipram, piclamilast, cilomilast and CDP-840.

Suitable antiimuscarinic agents include ipratropium bromide and tiatropium bromide.

Suitable H₁ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic-agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, amitriptyline, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, percocet, morphine sulfate, dilaudid, stadol, stadol NS, acetaminophen with codeine, acetaminophen with codeine #4, Lidoderm® patches, ziconotide, duloxetine, roboxetine, gabapentin and pregabalin.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for Inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

Yet another aspect of this invention is a compound of Formula I or a pharmaceutically acceptable ester, salt, prodrug or solvate thereof in isolated and purified form.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be anyalyzed for their composition and purity as well as characterized by standard analytical techniques such as, for example, elemental anyalysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, $^1$H spectra were obtained on either a Varian VXR-400 (400 MHz, $^1$H), Varian Gemini-300 (300 MHz), Varian Mercury VX-400 (400 MHz), or Bruker-Biospin AV-500 (500 MHz), and chemical shifts are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; t-Bu=tert-butyl; Ph=phenyl, and Ac=acetyl
μl=microliters
AcOEt or EtOAc=ethyl acetate
AcOH or HOAc=acetic acid
ACN=acetonitrile
atm=atmosphere
Boc=Di-tert-butyl dicarbonate
BINAP=2,2'-bis(diphenylphosphino)-1,1'-bisnaphthyl
CAT=catalyst
DEAD=diethylazodicarboxylate
DCM or $CH_2Cl_2$: dichloromethane:
DMAP=4-Dimethylaminopyridine
DIPEA=diisopropylethylamine
DMF=dimethylformamide
DMS=dimethylsulfide
DMSO=dimethyl sulfoxide
g=grams
h=hour
LCMS=liquid chromatography mass spectrometry
min=minute
mg=milligrams
mL=milliliters
mmol=millimoles
MeOH: methanol
MS=mass spectrometry
NBS=n-bromosuccimide
NMR=nuclear magnetic resonance spectroscopy
Pyr=pyridine
RT or rt=room temperature (ambient, about 25° C.).
TBSCl=t-butyldimethylsilyl chloride
TBS=t-butyldimethyl silyl
TEA or $Et_3N$=triethylamine
TEMPO=2,2,6,6-Tetramethylpiperidine-1-oxyl
TFA=trifluoroacetic acid
THF=tetrahydrofuran
TLC=thin layer chromatography
TMS=trimethylsilyl
Tos or tosyl=p-toluenesulfonyl
Tol=toluene
TOSMIC=Toluenesulfonylmethyl isocyanide
Tr=triphenylmethyl

EXAMPLES

The compounds of this invention can be prepared through the general approach outlined in Schemes 1-7. These schemes are being provided to illustrate the present invention. Group A is defined in these schemes in accordance with the definition in the invention; i.e., as an optionally substituted 5-membered heteroaryl, heterocyclyl or heterocyclenyl ring containing 1-3 heteroatoms. The depiction of A as an unsubstituted imidazole is not in any way to be considered a limitation of the invention scope. Likewise, the depiction of $J^1$-$J^3$ in some of the schemes as CH should not to be seen as a limitation in the scope of the invention; it would be within the skill level of the practitioner to prepare compounds where the variables are other than CH by modifying the schemes in the appropriate manner. Group P is an appropriate protecting group, the determination of which would be well within the skill level of one skilled in this art.

According to another embodiment (Scheme 3, wherein n=1-2), ketone S10 is converted to S18 by various olefination methods, such as, for example Wittig, Horner-Emmons, or Peterson reaction, or other related methods. Cyclopropanation of olefin S18 provides S19 via methods, such as a metal-catalyzed cyclopropanation with diazo compound. Conversion of S19 to S20 is achieved via one of the numerous heterocycle and heteroaryl synthetic methodologies that are known in the art (e.g., wherein A is an imidazole, S19 is converted to an aldehyde via a reduction and oxidation sequence, which is then treated with TosMIC/NaCN followed by $NH_3$ to afford S20). Compound S20 is then elaborated to S22 as described in Scheme 1.

The compounds of this invention can be prepared through the general approach outlined in Scheme 1. Ketone S1 (prepared according to literature precedent, Khimiya Geterotsiklicheskikh Soedinenii 1975, vol 8, 1118-1120) is converted to aldehyde S2 via one of numerous methods known to those skilled in the art including a Wittig-hydrolysis sequence (methoxymethyltriphenylphosphonium chloride/ PhLi, then HCOOH). Compound S3 (A-Y, wherein A=optionally protected imidazole, heteroaryl, heterocyclyl or heterocyclenyl and Y=I, Br, Cl or other appropriate group) is activated via Grignard or other metal-faciliated process and reacted with S2 to provide S4, which is subsequently dehydrated to provide alkene S5. The acetyl group is then removed and replaced with appropriate N-protecting group to give S6. The nitro group on S6 is reduced to aniline S7 with $SmI_2$ or other appropriate methods. Conversion of amino group to $R^1$ group provides compounds S8. Deprotection of compound S8 gives target compound S9. Removal of protecting group of A may be necessary depending on the nature of the group. For example, when A is a trityl or BOC-protected imidazole, deprotection under acidic conditions (TFA/$EtSi_3H$ or HCl/ MeOH) is undertaken.

SCHEME 1

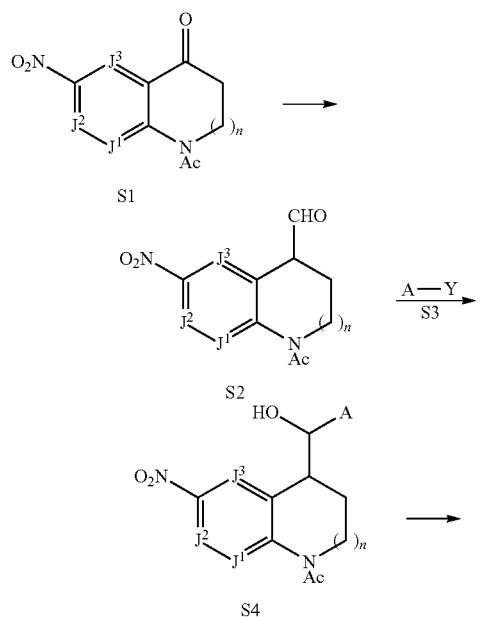

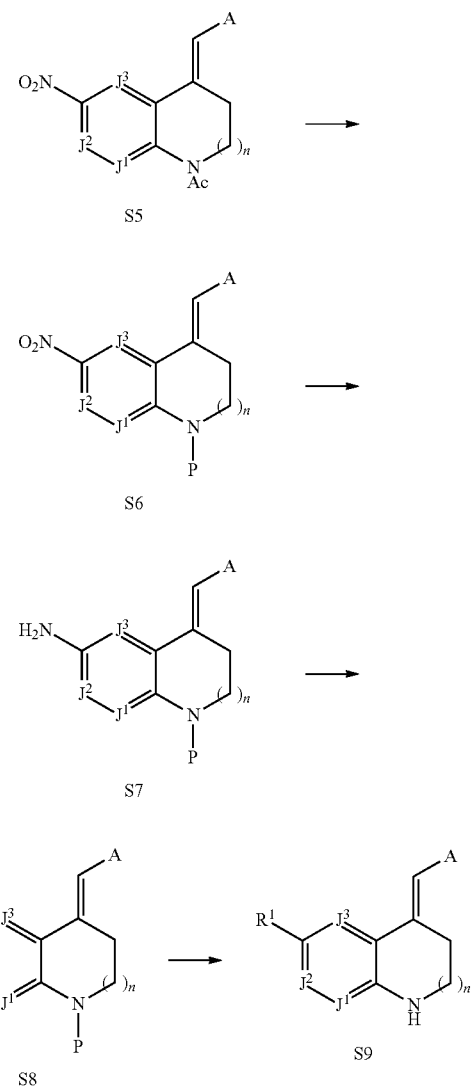

A = optionally protected imidazole, heteroaryl, heterocyclyl or heterocyclenyl
Y = I, Br, Cl or other appropriate group
P = appropriate protecting group According to another embodiment (Scheme 2, wherein n=1-2), compound S10 (prepared according to literature precedent, Journal of the Chemical Society, Perkin Transactions 1: Organic and Bio-Organic Chemistry 1980, vol 10, 2105-2111) is protected with appropriate N-protecting group to give S11. Ketone S11 is homologated to aldehyde S12 with various methods known to those skilled in the art, such as, for example a Wittig-hydrolysis sequence. Aldehyde S12 is then reacted with A-Y (wherein A=optionally protected imidazole, heteroaryl, heterocyclyl or heterocyclenyl and Y=I, Br, Cl or other appropriate group) via a Grignard or related metal-facilitated addition. The resulting alcohol S13 is oxidized to ketone S14. The resulting ketone S14 is converted to S15 by various known olefination methods, such as, for example Wittig, Horner-Emmons, Peterson reactions, or other related methods. Compound S15 is elaborated to S17 in a similar way as described in Scheme 1.

SCHEME 2

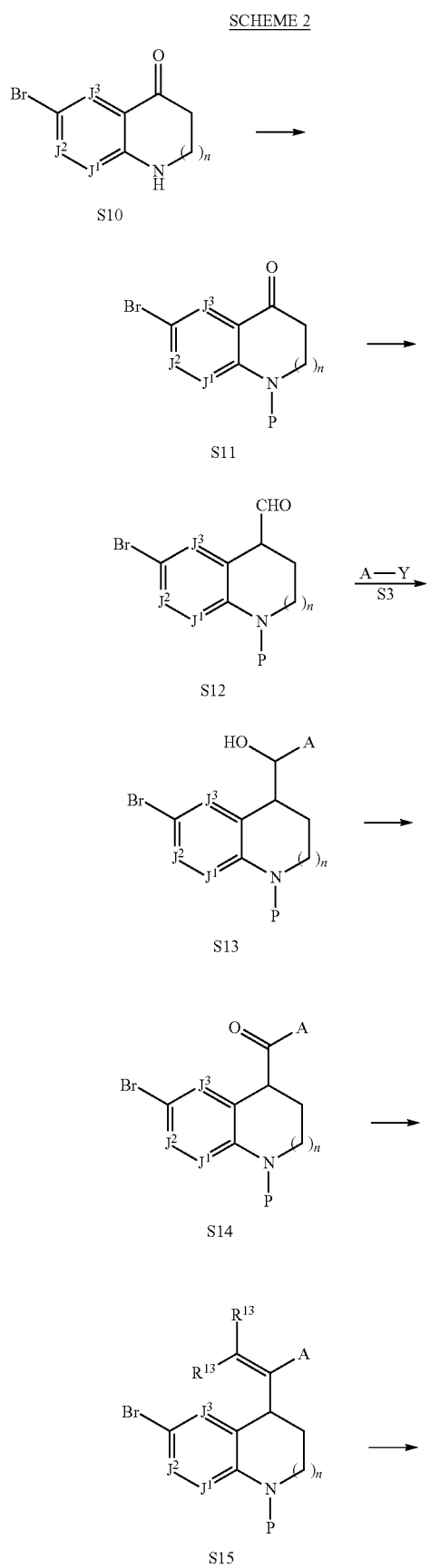

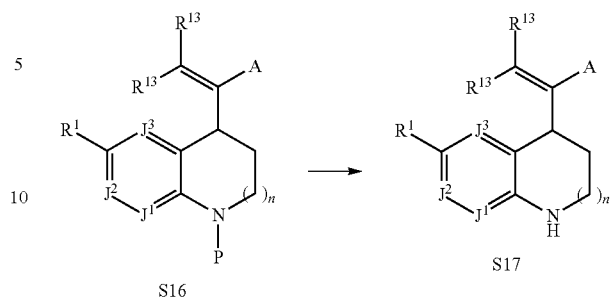

A = optionally protected imidazole, heteroaryl, heterocyclyl or heterocyclenyl
Y = I, Br, Cl or other appropriate group
P = appropriate protecting group According to another embodiment (Scheme 3, wherein n=1-2), ketone S11 is converted to S18 by various olefination methods, such as, for example Wittig, Horner-Emmons, or Peterson reaction, or other related methods. Cyclopropanation of olefin S18 provides S19 via methods, such as a metal-catalyzed cyclopropanation with diazo compound. Conversion of S19 to S20 is achieved via one of the numerous heterocycle and heteroaryl synthetic methodologies that are known in the art (e.g., wherein A is an imidazole, S19 is converted to an aldehyde via a reduction and oxidation sequence, which is then treated with TosMIC/NaCN followed by $NH_3$ to afford S20). Compound S20 is then elaborated to S22 as described in Scheme 1.

SCHEME 3

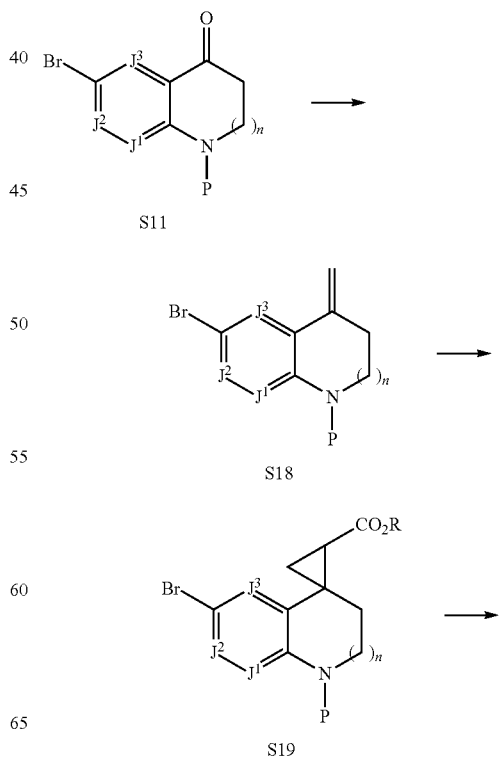

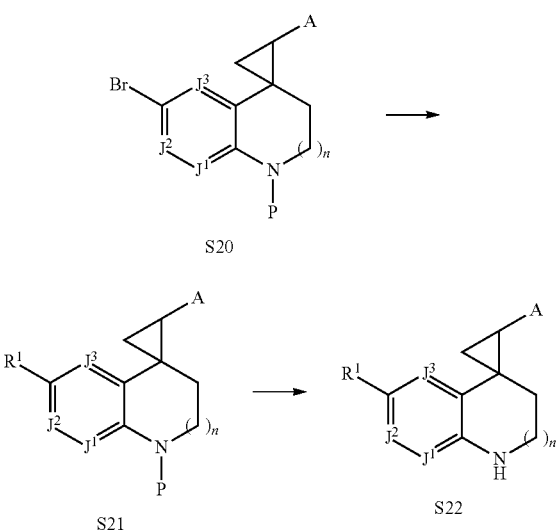

S20

S21

S22

A = optionally protected imidazole, heteroaryl, heterocyclyl or heterocyclenyl
P = appropriate protecting group According to another embodiment (Scheme 4), compound S23 is treated with A-CHO (wherein A=optionally protected imidazole, heteroaryl, heterocyclyl or heterocyclenyl) to afford S24, which is then treated with trimethylsulfoxonium iodide or the like. Final reduction with LAH or similar reducing agent provides S26.

SCHEME 4

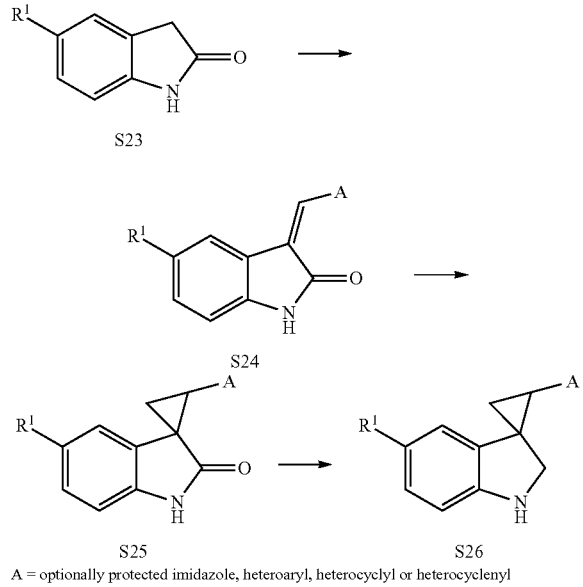

S23

S24

S25

S26

A = optionally protected imidazole, heteroaryl, heterocyclyl or heterocyclenyl

According to another embodiment (Scheme 5), compound S27 is converted to S28 (R=CO$_2$Me) as described in the literature (for example, for P=BOC, see Bioorganic & Medicinal Chemistry Letters (1996), 6(22), 2741-2744). The methyl ester is then converted to Weinreb amide S29 by methods well known to those skilled in the art (for example, sequential saponification with LiOH and amide coupling with N-methoxymethylamine; alternatively direct conversion with N-methoxymethylamine and trimethylaluminum). Compound S29 is then reacted with A-Y (wherein A=optionally protected imidazole, heteroaryl, heterocyclyl or heterocyclenyl and Y=I, Br, Cl or other appropriate group) via a Grignard or related metal-facilitated addition. The resulting ketone S30 is converted to S31 by a known olefination method (such as, for example, Wittig, Horner-Emmons, or Peterson reaction, or similar methods know to those skilled in this art), followed by final deprotection. For example, when P=BOC, acidic conditions (TFA/EtSi$_3$H or HCl/MeOH) are used.

SCHEME 5

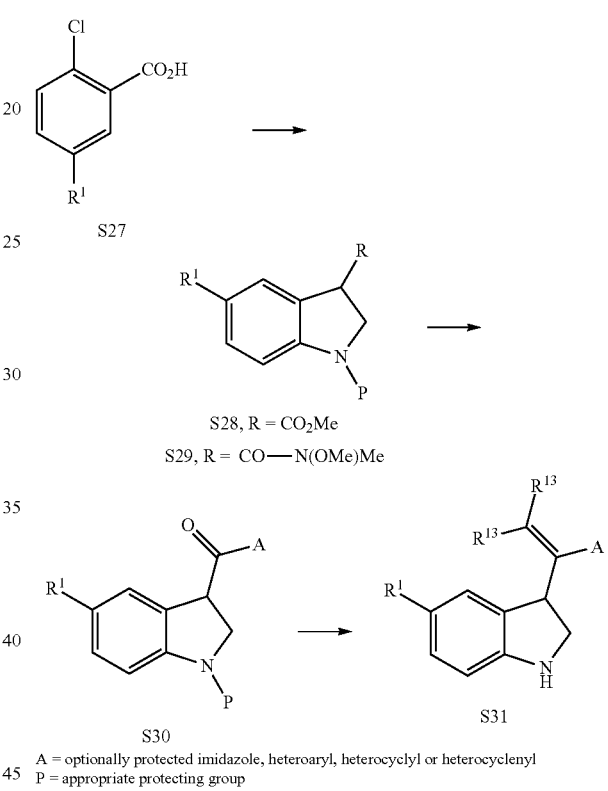

S27

S28, R = CO$_2$Me

S29, R = CO—N(OMe)Me

S30

S31

A = optionally protected imidazole, heteroaryl, heterocyclyl or heterocyclenyl
P = appropriate protecting group According to another embodiment (Scheme 6), compound S32 (wherein R=Br or other appropriate leaving group) is converted to S33 (R═SPh) by nucleophilic displacement or other related chemistry. Compound S34 is then subject to Wittig, Horner-Emmons, or other known olefination procedures with a reagent such as, for example, (triphenylphosphanylidene)acetic acid ethyl ester. Following reduction of the ester group and subsequent conversion to an appropriate leaving group (such as, for example, mesylate, tosylate, bromide, chloride or related), compound S35 is treated with an appropriately substituted aniline S36, wherein R═H or appropriate protecting group, to provide S37. In a manner similar to that described in the literature (see for example, Tetrahedron Letters, 1982, 23, 2575 and Journal of the American Chemical Society, 1990, 112, 5230), S37 undergoes a radical cyclization facilitated by appropriate reagents, such as, for example Bu$_3$SnH/AIBN, or the like. Final deprotection of the indoline nitrogen and/or the A heterocycle may be done as appropriate to provide S38.

SCHEME 6

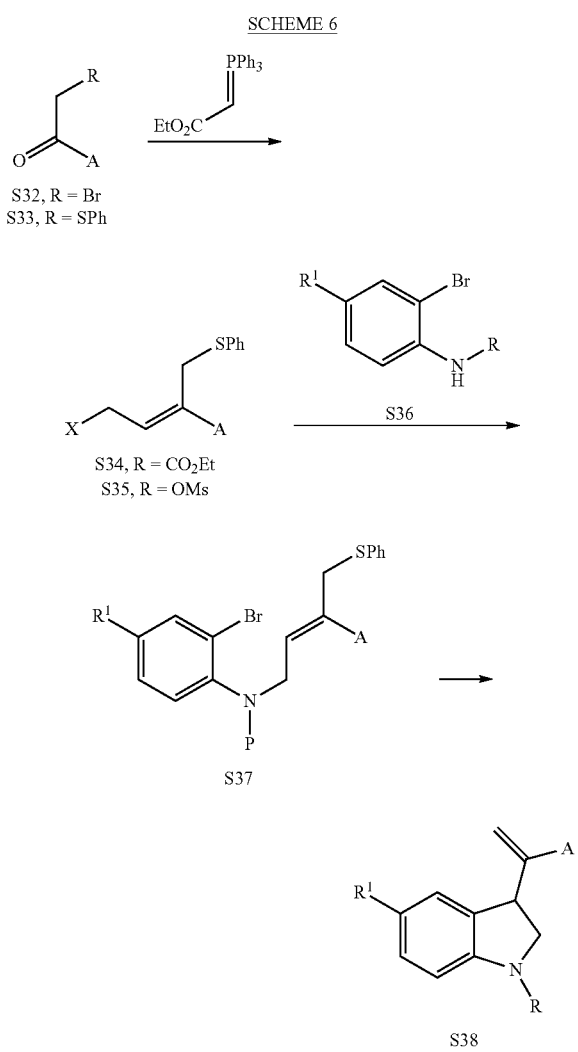

A = optionally protected imidazole, heteroaryl, heterocyclyl or heterocyclenyl
P = appropriate protecting group

SCHEME 7

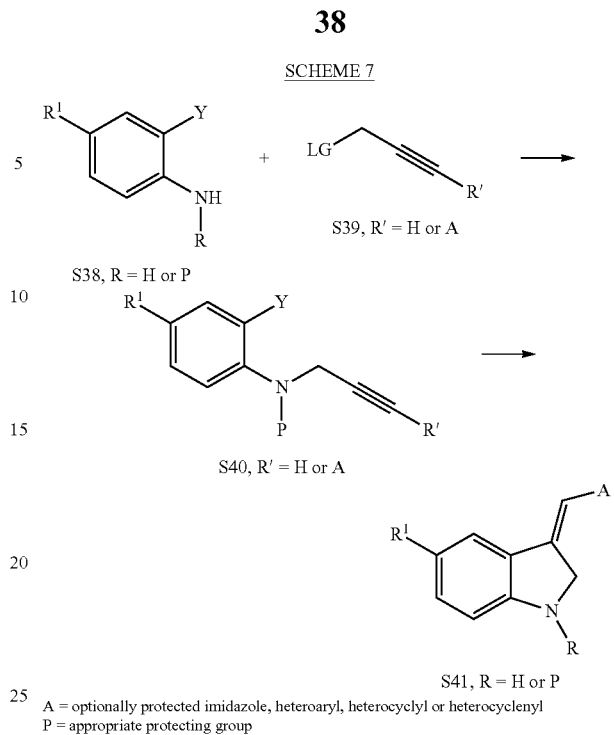

A = optionally protected imidazole, heteroaryl, heterocyclyl or heterocyclenyl
P = appropriate protecting group The starting materials and reagents described herein for preparing compounds described are either available from commercial suppliers such as Aldrich Chemical Co. (Wisconsin, USA) and Acros Organics Co. (New Jersey, USA) or are prepared by literature methods known to those skilled in the art.

Exemplary compounds are prepared as described in the examples below or from starting materials that are known in the art. These examples are being provided to further illustrate the present invention. They are for illustrative purposes only; the scope of the invention is not to be considered limited in any way thereby.

Example 1

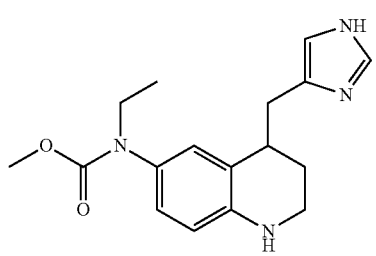

Step 1

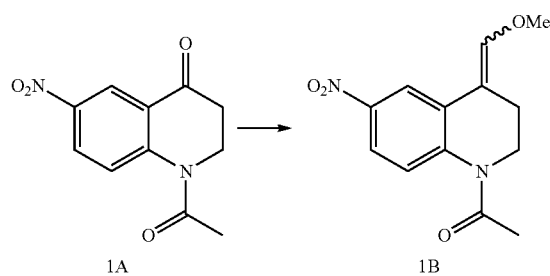 [SMILES: CC(=O)N1CCC(=O)c2cc([N+](=O)[O-])ccc21 ; COC=C1CCN(C(C)=O)c2ccc([N+](=O)[O-])cc21]

According to another embodiment (Scheme 7), compound S38 (wherein R═H or a protecting group; Y═Br or I) is treated with S39 (wherein LG=an appropriate leaving group, such as, for example Cl, Br, or OMs and wherein R'═H or A, an optionally protected imidazole, heteroaryl, heterocyclyl or heterocyclenyl group). The resulting compound S40 (R═A) may undergo a radical cyclization facilitated by appropriate reagents, such as Bu$_3$SnH/AIBN (see for example Synlett 2001, 8, 1287) or the like. Alternatively, cyclization (R═A) may be affected by Pd catalysis (see, for example, Tetrahedron Letters, 1988, 29, 4325), photochemistry (see, for example, Synlett, 2005, 2248), Cr catalysis (see, for example, Tetrahedron Letters, 1994, 35, 1601), indium catalysis (see, for example Advanced Synthesis and Catalysis, 2005, 347, 1632) or other related methods. In another embodiment (R'═H), cyclization is affected by a palladium catalyst and then intercepted by a organozinc reagent A-ZnCl or organoboron reagent A-B(OR)$_2$ (wherein A is 1-tritylimidazol-4-yl, or another optionally protected imidazole or heteroaryl group; see for example, Tetrahedron Letters, 1989, 30, 1135). Final deprotection of the indoline nitrogen and/or the A heterocycle may be done as appropriate to provide S41.

To a suspension of methoxymethyltriphenylphosphonium chloride (34.8 g, 0.102 mol) in THF (350 ml) was added PhLi (1.8M in tButylether, 56.4 mL, 0.102 mol) slowly at −25° C. The mixture was stirred at −25° C. for 1 h, cooled to −78° C. A suspension of 1A (19.8 g, 0.085 mol, prepared according to the procedure published *Khimiya Geterotsiklicheskikh Soedinenii* 1975 (8), 1118-20) in THF (300 mL) was added slowly. The mixture was warmed up to RT and stirred for 1 h. The reaction was quenched with saturated NaHCO₃, diluted with EtOAc. The organic layer was washed with 1N NaOH, dried over MgSO₄, filtered and concentrated in vacuo. Flash chromatography (EtOAc/Hexane 1:1) afforded 1B (10.3 g).

Step 2

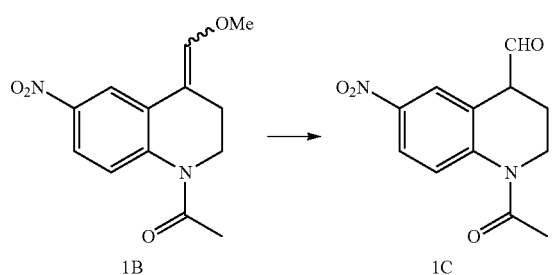 [SMILES: COC=C1CCN(C(C)=O)c2ccc([N+](=O)[O-])cc21 ; CC(=O)N1CCC(C=O)c2cc([N+](=O)[O-])ccc21]

1B (10.3 g, 0.0393 mol) was stirred in HCOOH (90%, 150 mL) at 90° C. for 2 h. The mixture was cooled down to RT, diluted with DCM and H₂O. The DCM layer was separated, washed with saturated NaHCO₃ (2×), brine, dried and concentrated to give 1C (8 g).

Step 3

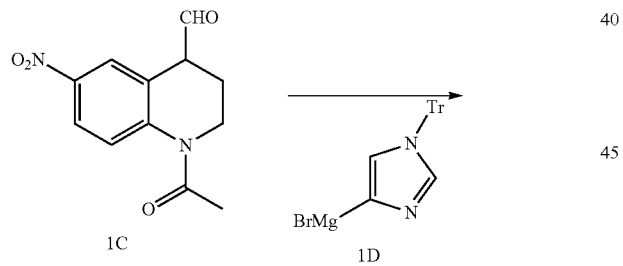

To a solution of 4-iodo-1-trityl-imidazole (12.4 g, 0.042 mol) in DCM (250 mL) was added EtMgBr (3.0M in Et₂O, 14.1 mL, 0.042 mol) slowly at −20° C., stirred at 0° C. for 30 min. A solution of 1C (7 g, 0.028 mol) in DCM (100 mL) was added very slowly. The mixture was stirred at RT for 1 h, quenched with saturated NaHCO₃, diluted with DCM. The DCM layer was washed with brine, dried and concentrated. Flash chromatography (EtOAc) afforded 1F (8.0 g).

Step 4

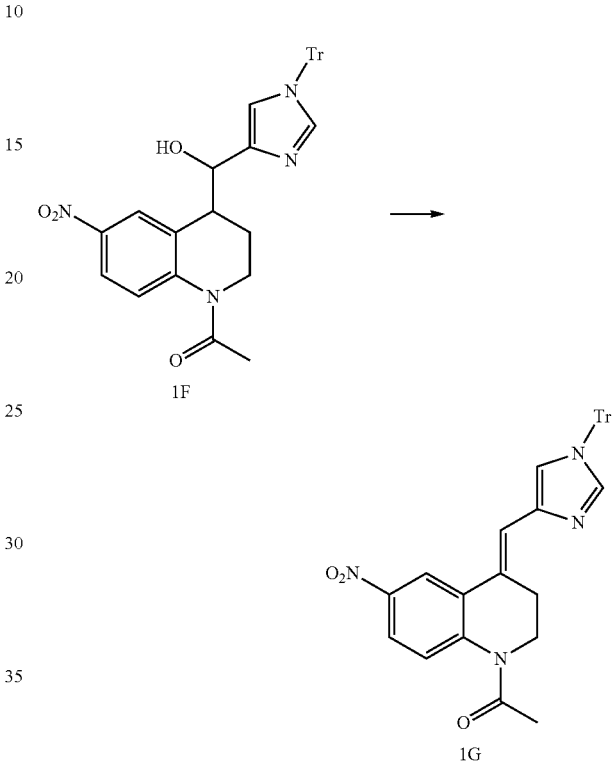

To a solution of 1F (8.0 g, 0.014 mol) in DCM (300 mL) was added Et₃N (4.33 g, 0.043 mol), followed by dropwise addition of MsCl (1.98 g, 0.017 mol) at RT. The mixture was stirred at RT for 1 h. DBU (17.4 g, 0.114 mol) was added in one portion. The mixture was stirred in a pressure flask at 65° C. for 2 h, cooled down to RT, concentrated in vacuo. Flash chromatography (EtOAc/Hexane 2:1) afforded 1G (3.2

Step 5

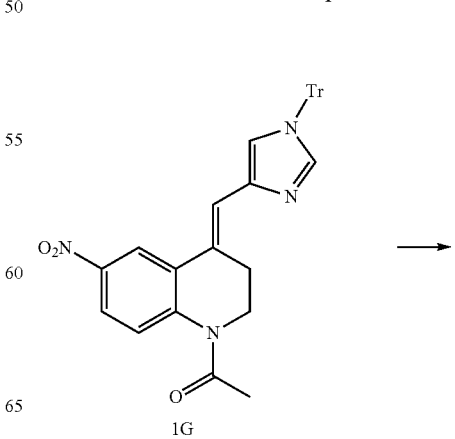

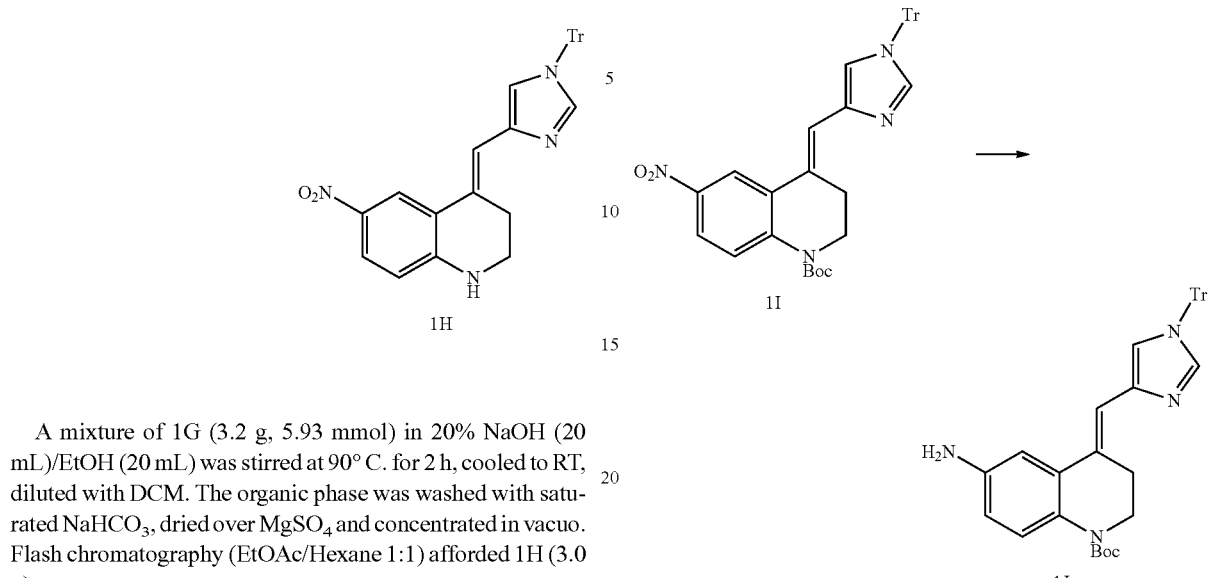

A mixture of 1G (3.2 g, 5.93 mmol) in 20% NaOH (20 mL)/EtOH (20 mL) was stirred at 90° C. for 2 h, cooled to RT, diluted with DCM. The organic phase was washed with saturated NaHCO₃, dried over MgSO₄ and concentrated in vacuo. Flash chromatography (EtOAc/Hexane 1:1) afforded 1H (3.0 g).

Step 6

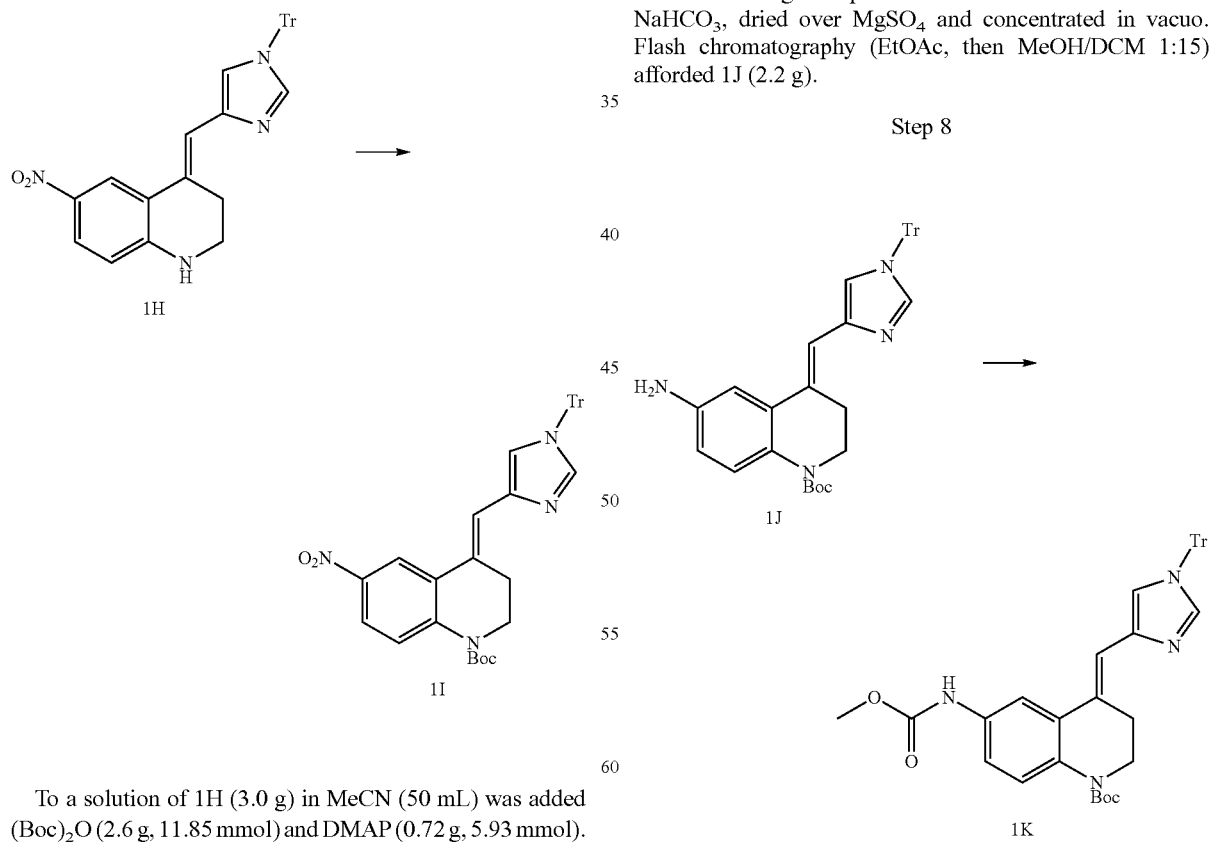

To a solution of 1H (3.0 g) in MeCN (50 mL) was added (Boc)₂O (2.6 g, 11.85 mmol) and DMAP (0.72 g, 5.93 mmol). The mixture was stirred at RT for 18 h. The mixture was diluted with DCM, washed with saturated NaHCO₃, dried over MgSO₄ and concentrated in vacuo. Flash chromatography (EtOAc/Hexane 1:1) afforded 1I (3.0 g).

Step 7

To a stirred suspension of 1I (3.0 g, 5 mmol) in THF (60 mL)/MeOH (120 mL) at RT was added SmI₂ solution (0.1 M in THF) until the deep blue color persist. The reaction mixture was diluted with Et₂O and H₂O, filtered through a pad of celite. The organic phase was washed with saturated NaHCO₃, dried over MgSO₄ and concentrated in vacuo. Flash chromatography (EtOAc, then MeOH/DCM 1:15) afforded 1J (2.2 g).

Step 8

To a solution of 1J (500 mg, 0.88 mmol) and Et₃N (178 mg, 1.76 mmol) in DCM at −78° C. was added slowly methylchloroformate (92 mg, 0.97 mmol). The stirring mixture was slowly warmed up to 0° C., diluted with DCM, washed with saturated NaHCO$_3$, dried over MgSO$_4$ and concentrated in vacuo. Flash chromatography (EtOAc/Hex 2:1, then EtOAc, then MeOH/DCM 1:15) afforded 1K (250 mg).

Step 9

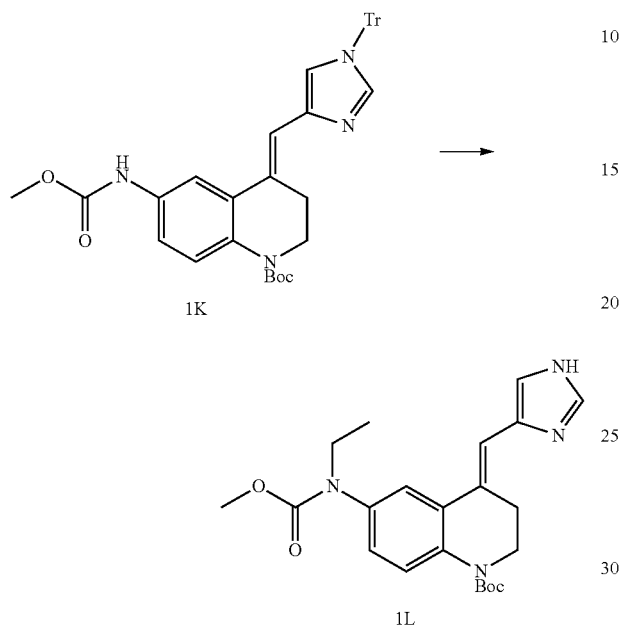

To a solution of 1K (40 mg, 0.064 mmol) in acetone (2 mL) was added EtI (40 mg, 0.256 mmol) and dry Cs$_2$CO$_3$ (40 mg). The mixture was stirred at 50° C. for 18 h, diluted with DCM, filtered and concentrated in vacuo. Flash chromatography (EtOAc/Hex 2:1) afforded 1L (24 mg)

Step 10

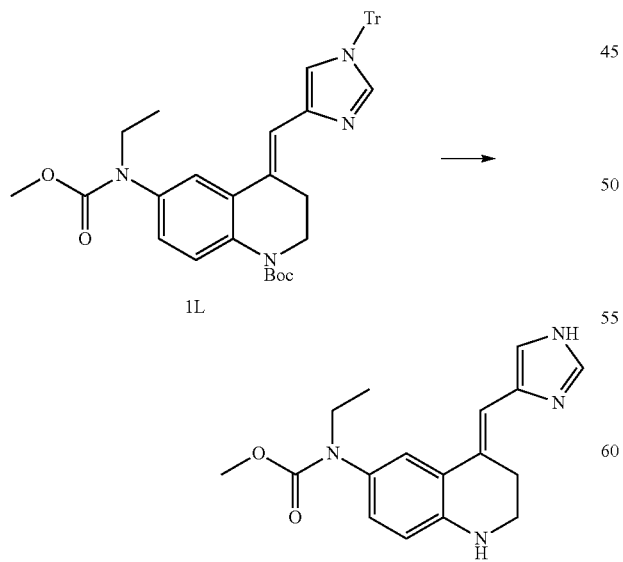

Compound 1L (24 mg) was dissolved in DCM (2 mL) and TFA (2 mL). Et$_3$SiH (4 mg, 0.044 mmol) was added. The mixture was stirred for 3 h at RT, concentrated in vacuo. Preparative TLC (MeOH (7N NH$_3$)/DCM, 1:10) afforded 1 (8 mg MS MH+ 313).

In a similar manner that described above, the following compounds were synthesized from 1J by using the indicated reagents:

| Cpd | Reagent | R | MS (MH+) |
|---|---|---|---|
| 1M | MeNCO | | 312 |
| 1N | Acetyl chloride, Et$_3$N | | 297 |
| 1O | Propionyl, Et$_3$N | | 311 |

Example 2

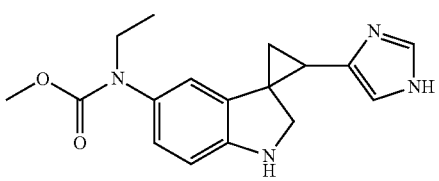

Steps 1-2

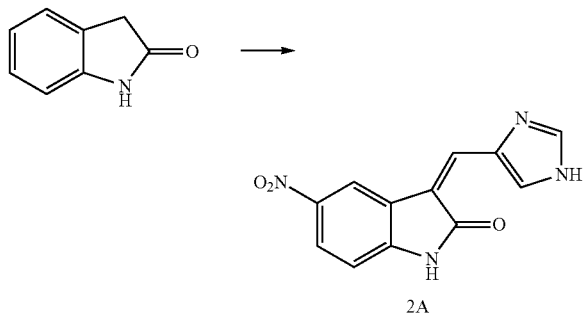

2-indolinone (12 g) was nitrated (40 mL AcOH, 5 mL HNO$_3$) in a manner similar to that described in PCT WO 2001037820. The resulting compound, 5-nitro-2-indolinone, was taken up in EtOH (250 mL) and treated with imidazole-4-carbaldehyde (1 eq) and NaOH (~10 g). The mixture was stirred at room temperature overnight, neutralized with HCl, and concentrated. The residue was then absorbed onto silica gel and subjected to chromatography (0.25% NH$_4$OH/10% MeOH in DCM) to provide 2A as a brown solid. MS m/z 257 (MH$^+$).

Step 3

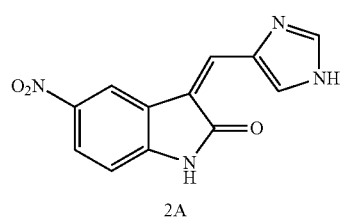
2A

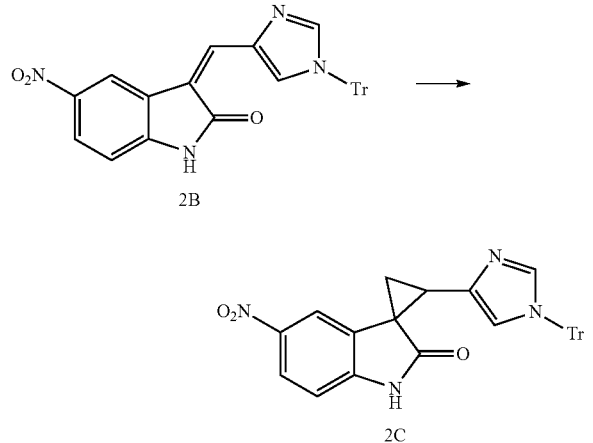
2B

A mixture of compound 2A (1 g), trityl chloride (1 eq), and Et$_3$N (2 mL) in DMF (20 mL) was stirred overnight and then concentrated. The residue was taken up in DCM (50 mL), washed with aq. NaOH, dried over Na$_2$SO$_4$, filtered, and concentrated to provide 2B in quantitative yield.

Step 4

2B

2C

In a manner similar to that described in WO 2007/008664, compound 2B is treated with trimethylsulfoxonium iodide and NaH in DMSO to provide 2C.

Steps 5-6

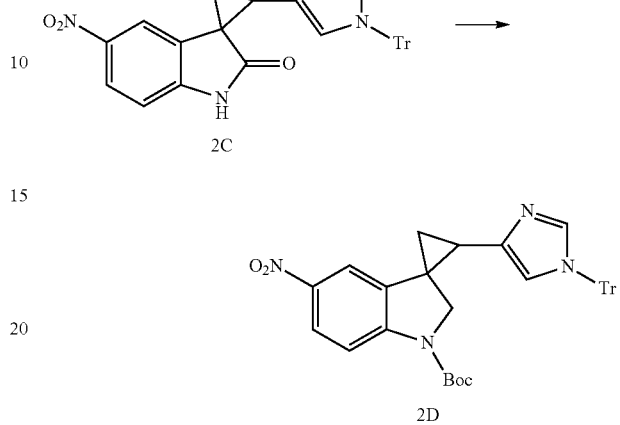
2C

2D

A mixture of compound 2C in THF is treated slowly with BH$_3$-DMS (2.0 M/THF) at RT and then heated as needed. The reaction mixture is concentrated, treated with K$_2$CO$_3$ and EtOH, and then stirred overnight at RT. The reaction mixture is filtered, concentrated, added to H$_2$O and extracted with CH$_2$Cl$_2$ (4×). The combined organic layers are dried with Na$_2$SO$_4$, filtered and concentrated. The resulting indoline is then protected with Boc$_2$O and catalytic DMAP as described in Example 1 (Step 5) to provide 2D.

Steps 7-8

2D

2E

The nitro group in compound 2D is reduced by a method known in the literature (such as SnCl$_2$, catalytic hydrogenation or the like) and then acetylated with acetic anhydride or acetyl chloride and an appropriate base (such as DIPEA or Et$_3$N) to provide 2E.

Steps 9-11

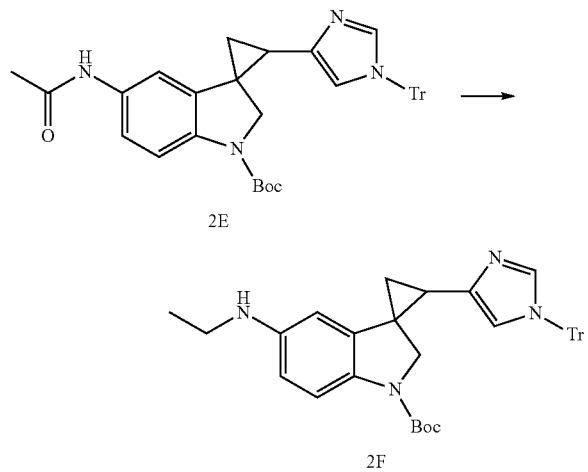

Compound 2E is reduced with LAH to provide 2F. In a manner similar to that found in Example 1 (Steps 7-8), 2F is sequentially treated with ClCO$_2$Me and DIPEA and then globally deprotected with TFA/Et$_3$SiH to provide the title compound 2.

Example 3

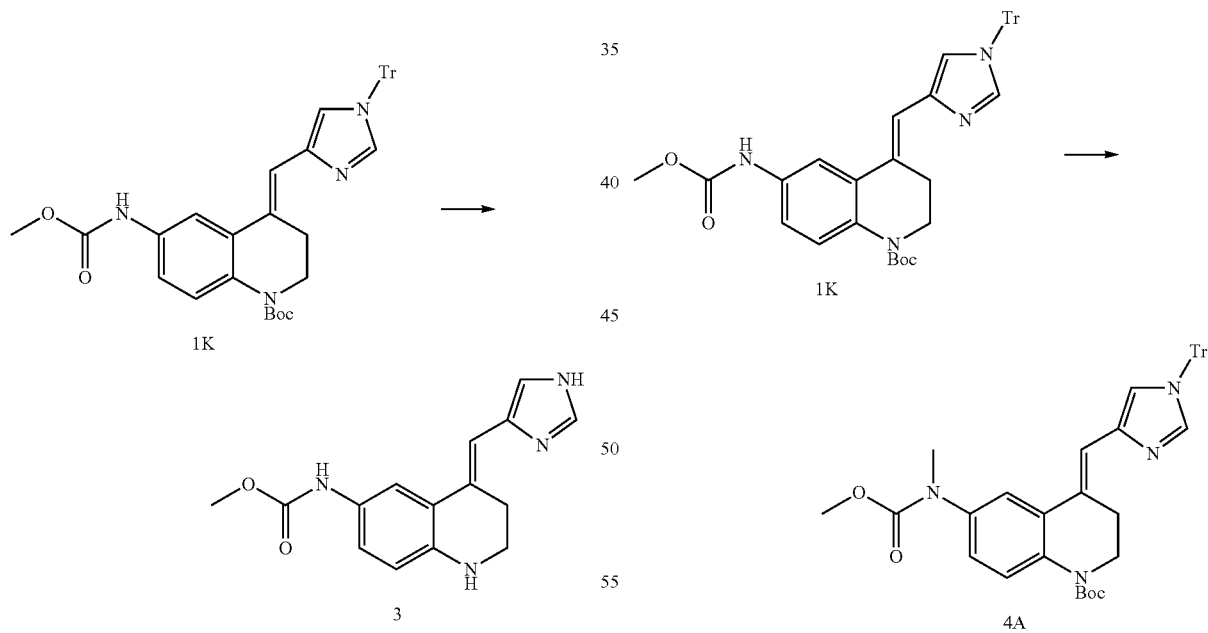

Compound 1K (24 mg, 0.038 mmol) was dissolved in DCM (2 mL) and TFA (2 mL). Et$_3$SiH (0.05 mL) was added. The mixture was stirred for 3 h at RT, concentrated in vacuo. Preparative TLC (MeOH (7N NH$_3$)/DCM, 1:10) afforded 3 (6 mg, MH$_+$ 285).

In a similar manner that described in Example 1 and above, the following compounds were synthesized from 1J by using the indicated reagents:

| Cpd | Reagent | R | MS (MH+) |
|---|---|---|---|
| 3L | MeNCO | methylurea | 284 |
| 3M | Acetic chloride, Et$_3$N | acetamide | 269 |
| 3N | Propionyl chloride, Et$_3$N | propionamide | 283 |

Example 4

Step 1

To a suspension of NaH (60% in mineral oil, 15 mg, 0.383 mmol) in THF (4 mL) was added a solution of 1K (80 mg, 0.128 mmol) in THF (1 mL), followed by MeI (0.5 mL). The mixture was stirred at RT for 1 h, quenched with saturated NaHCO$_3$, diluted with DCM, filtered and concentrated in vacuo. Flash chromatography (EtOAc/Hex 2:1) afforded 4A (60 mg).

49

Step 2

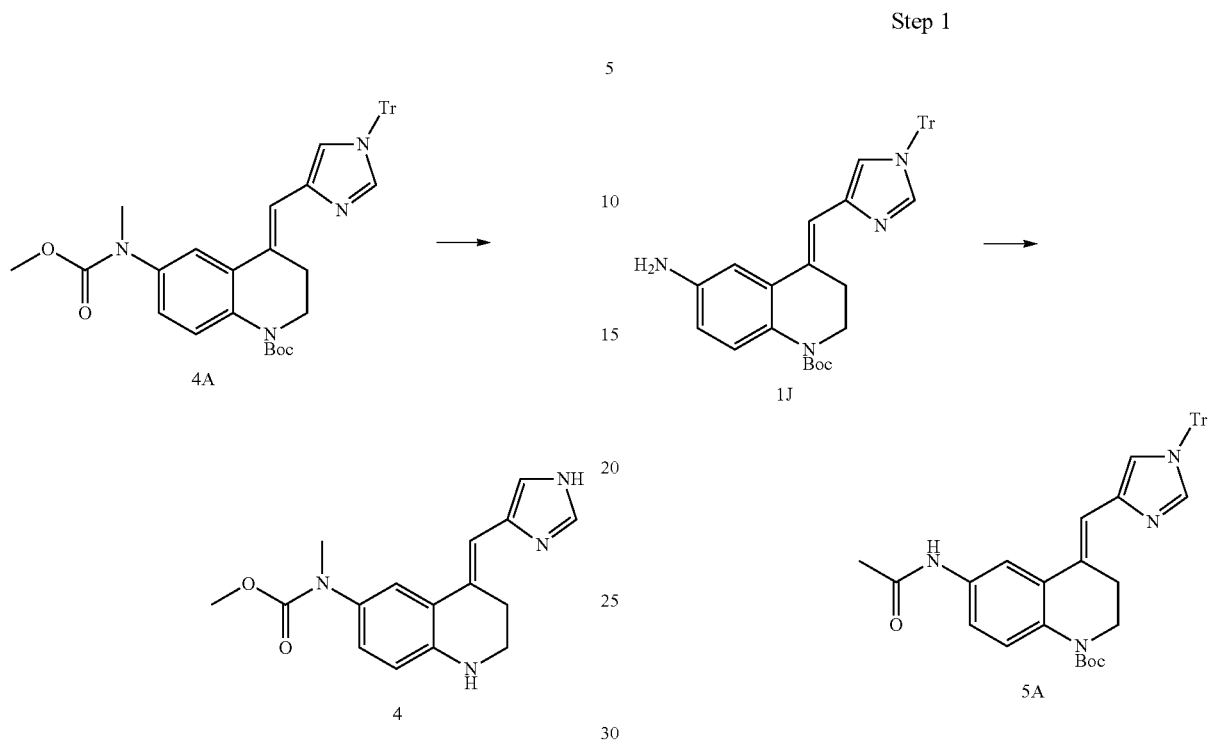

Compound 4A (60 mg) was dissolved in DCM (2 mL) and TFA (2 mL). Et₃SiH (0.1 mL) was added. The mixture was stirred for 2 h at RT, concentrated in vacuo. Preparative TLC (MeOH (7N NH₃)/DCM, 1:10) afforded 4 (22 mg, MS MH+299).

In a similar manner that described in example 1 and above, the following compounds were synthesized from 1J by using the indicated reagent:

| Cpd | Reagent | R | MS (MH+) |
|---|---|---|---|
| 4B | MeNCO | | 298 |
| 4C | Acetic chloride, Et₃N | | 283 |
| 4D | Propionyl chloride, Et₃N | | 297 |

50

Example 5

Step 1

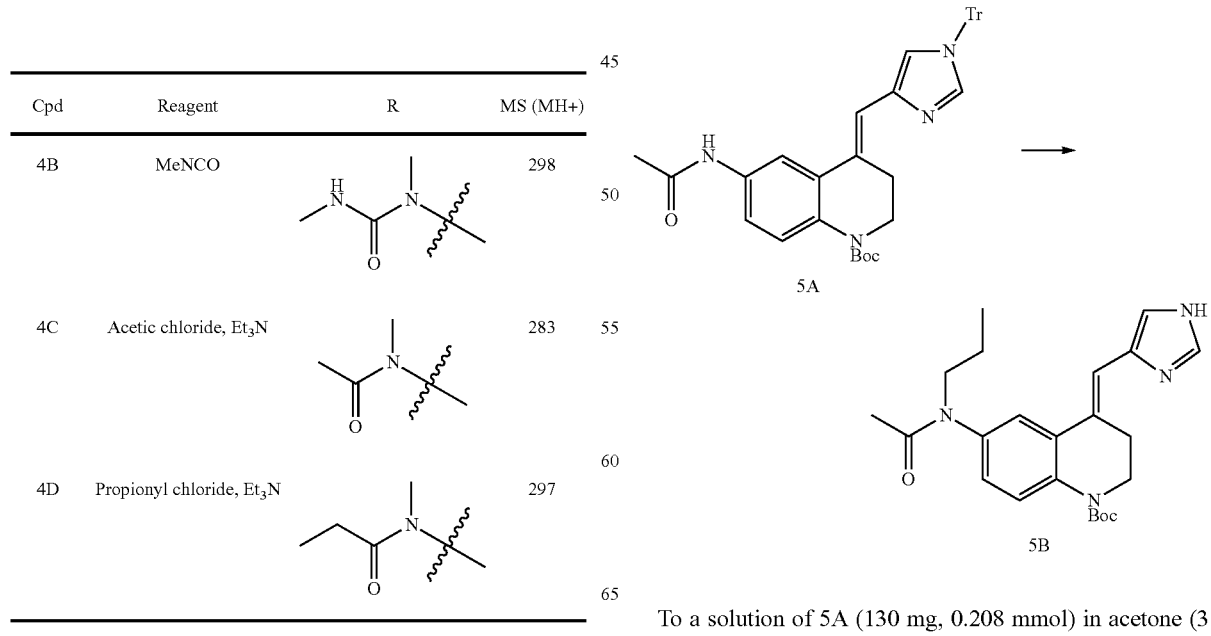

To a solution of 1J (400 mg, 0.852 mmol) and Et₃N (173 mg, 1.70 mmol) in DCM (10 mL) at RT was added slowly AcCl (73 mg, 0.937 mmol) in DCM (1 mL). The stirring mixture was stirred for 1 h, diluted with DCM, washed with saturated NaHCO₃, dried over MgSO₄ and concentrated in vacuo. Flash chromatography (EtOAc/Hex 9:1) afforded 5A (350 mg).

Step 2

To a solution of 5A (130 mg, 0.208 mmol) in acetone (3 mL) was added PrI (106 mg, 0.623 mmol) and dry Cs₂CO₃

(100 mg). The mixture was stirred at 50° C. for 18 h, diluted with DCM, filtered and concentrated in vacuo to afford 5B (96 mg)

Step 3

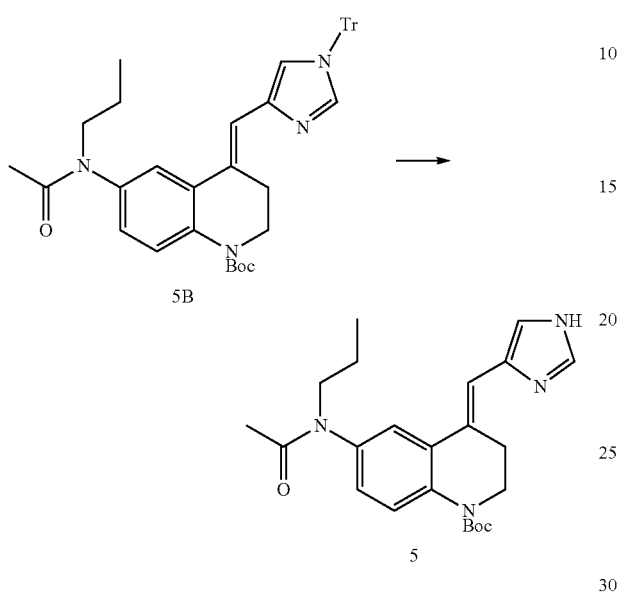

5B

Compound 5B (96 mg, 0.147 mmol) was dissolved in DCM (5 mL) and TFA (5 mL). Et$_3$SiH (27 mg, 0.294 mmol) was added. The mixture was stirred for 3 h at RT, concentrated in vacuo. Preparative TLC (MeOH (7N NH$_3$)/DCM, 1:10) afforded 5 (40 mg, MS MH+ 311).

Example 6

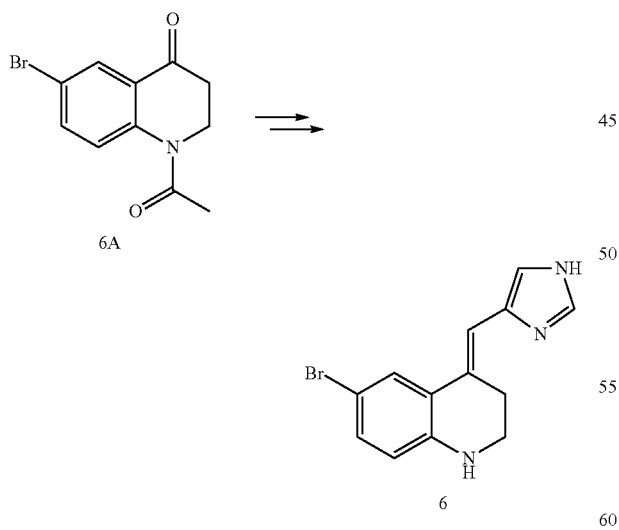

6A

6

In a similar manner that described in example 1, compound 6 were synthesized by using 6A as the starting material:
Assay:

Efficacy agonist activity values (Emax, GTPγS assay) for α2A and α2C were determined by following the general procedure detailed by Umland et. α1 ("Receptor reserve analysis of the human α$_{2C}$-adrenoceptor using [$^{35}$S]GTPγS and cAMP functional assays" European Journal of Pharmacology 2001, 411, 211-221). For the purposes of the present invention, a compound is defined to be a specific or at least functionally selective agonist of the α2C receptor subtype if the compound's efficacy at the α2C receptor is ≧30% Emax (GTPγS assay) and its efficacy at the α2A receptor is 30% Emax (GTPγS assay).

The following compounds were evaluated to be specific or at least selective agonists of the α2C receptor subtype based on the previously defined definition: 1, 1M, 1N.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound of Formula II

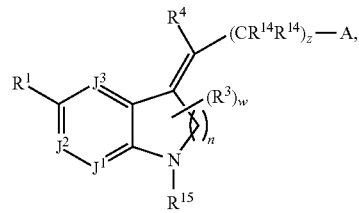

Formula II wherein
J$^1$, J$^2$, and J$^3$ are independently —N— or —C(R$^2$)—;
A is

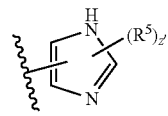

R$^1$ is —[C(R$^a$)(R$^b$)]$_g$N(R$^7$)YR$^7$', wherein R$^a$ and R$^b$ are independently selected from the group consisting of H, alkyl, alkoxy, and halo
Y is —C(=O)—, —C(=O)O— or —C(=O)NR$^7$;
z' is 1 or 2; and
n is 2,
R$^2$ is independently selected from the group consisting of —H, —OH, halo, —CN, —NO$_2$, —S(O)$_p$R$^7$, —NR$^7$R$^7$', —[C(R$^a$)(R$^b$)]$_g$YR$^7$', —[C(R$^a$)(R$^b$)]$_q$N(R$^7$)YR$^7$', —[C(R$^a$)(R$^b$)]=$_q$OYR$^7$', and —(CH$_2$)$_q$ON=CR$^7$R$^7$', and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$;
R$^3$ is independently selected from the group consisting of H, halo, and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one R$^5$, provided that when w is 3, no more than 2 of the R$^3$ groups may be (=O);
R$^4$ is independently selected from the group consisting of H, halo, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —NO$_2$, —NR$^7$R$^{7'}$, and —S(O)$_p$R$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents and/or 1 or 2 (=O);

$R^7$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$;

$R^{7'}$ is independently selected from the group consisting of H and alkyl, alkenyl, alkynyl, cycloalkyl, cycloalkylalkyl, cycloclenyl, cyclocyclenylalkyl, aryl, arylalkyl, heterocyclyl, heterocyclylalkyl, hetrocyclenyl, hetrocyclenylalkyl, heteroaryl, and heteroarylalkyl groups, each of which is optionally substituted one or more times by $R^{12}$; or a) when a variable is —NR$^7$R$^{7'}$, —[C(R$^a$)(R$^b$)]$_q$YR$^{7'}$, —C[(R$^a$)(R$^b$)]$_q$NR$^7$R$^{7'}$, —[C(R$^a$)(R$^b$)]$_q$OYR$^{7'}$, —(CH$_2$)$_g$NR$^7$R$^{7'}$, —C(O)NR$^7$R$^{7'}$ or —SO$_2$NR$^7$R$^{7'}$, $R^7$ and $R^{7'}$ together with the nitrogen atom to which they are attached independently form a 3- to 8-membered heterocyclyl, heterocyclenyl or heteroaryl ring having, in addition to the N atom, 1 or 2 additional hetero atoms independently selected from the group consisting of O, N, —N(R$^9$)— and S, wherein said rings are optionally substituted by 1 to 5 independently selected $R^5$ moieties and/or 1 or 2 (=O), or b) when a variable is —(CH$_2$)$_q$ON=CR$^7$R$^{7'}$ or —[C(R$^a$)(R$^b$)]$_q$ON=CR$^7$R$^{7'}$, $R^7$ and $R^{7'}$ together with the carbon atom to which they are attached independently form a 3- to 8-membered cycloalkyl, cycloalkenyl, aryl, heterocyclyl, heterocyclenyl or heteroaryl ring, wherein said hetroacyclyl, heterocyclenyl or heteroaryl rings have 1-3 heteroatoms which are independently selected from the group consisting of O, N, —N(R$^9$)— and S, wherein said rings are optionally substituted by 1 to 5 independently selected $R^5$ moieties and/or 1 or 2 (=O);

$R^9$ is independently selected from the group consisting of H, —C(O)—R$^{10}$, —C(O)—OR$^{10}$, and —S(O)$_p$—OR$^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O);

$R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —S(O)$_p$R$^{11}$ substituents and/or 1 or 2 (=O);

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl, each of which is optionally substituted by at least one substituent independently selected from the group consisting of halo, —OH, —CN, —NO$_2$, —N(R$^{11'}$)$_2$, and —S(O)$_p$R$^{11}$ substituents and/or 1 or 2 (=O);

$R^{11'}$ is independently selected from the group consisting of H, alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

$R^{12}$ is independently selected from the group consisting of H, halo, —OH, —CN, —NO$_2$, —N(R$^{11}$)$_2$, and —S(O)$_p$R$^{11}$, and/or 1 or 2 (=O), and alkyl, alkoxy, alkenyl, alkenyloxy, alkynyl, cycloalkyl, cycloalkoxy, aryl, aryloxy, arylalkyl, heteroaryl, heteroaryloxy, heteroarylalkyl, heterocyclyl, heterocyclenyl, heterocyclenyloxy, heterocyclylalkyl, heterocyclenylalkyl, arylalkoxy, heteroarylalkoxy, heterocyclylalkoxy, and heterocyclenylalkoxy groups, each of which in turn is optionally substituted by at least one by a substituent selected from the group consisting of H, alkyl, haloalkyl, halo, —OH, optionally substituted alkoxy, optionally substituted aryloxy, optionally substituted cycloalkoxy, optionally substituted heteroaryloxy, optionally substituted heterocyclenyloxy, —CN, —NO$_2$, —N(R$^{11}$)$_2$, and —S(O)$_p$R$^{11}$ and/or 1 or 2 (=O), wherein said optionally substituted alkoxy, aryloxy, optionally substituted cycloalkoxy, optionally substituted heteroaryloxy, and heterocyclenyloxy when substituted are substituted one or more times by $R^{11}$;

$R^{14}$ is independently selected from the group consisting of H, alkyl, halo, —CN, and alkoxy, $R^{15}$ is selected from the group consisting of H, —C(O)—R$^{10}$, and —S(O)$_p$OR$^{10}$ and alkyl, alkenyl, cycloalkyl, aryl, arylalkyl, heteroaryl, and heteroarylalkyl groups, each of which is optionally substituted with at least one halo, —OH, —CN, —NO$_2$, —N(R$^{11}$)$_2$, and —S(O)$_p$R$^{11}$ and/or 1 or 2 (=O);

w is 0, 1, 2, 3, or 4;
p is independently 0, 1 or 2;
q is independently an integer from 0-10;
z is 0, 1, 2 and
or a pharmaceutically acceptable salt, solvate, ester or prodrug thereof.

2. The compound according to claim 1, which has the formula

Formula IIa wherein
n is 2;
$J^1$ is CH;
$J^2$ is CH;
$J^3$ is CH;
$R^1$ is —[C(R$^a$)(R$^b$)]$_q$N(R$^7$)YR$^{7'}$
Y is —C(=O)—, —C(=O)O— or —C(=O)NR$^7$
z' is 1 or 2;
$R^4$ is H;
$R^5$ is H;

$R^7$ is independently H, alkyl, cycloalkyl, or arylalkyl;
$R^{7'}$ is H or alkyl; and
w is 0
or a pharmaceutically acceptable salt, solvate, ester or prodrug thereof.
3. A compound which is
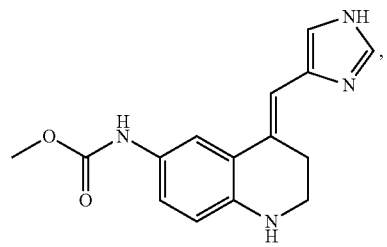
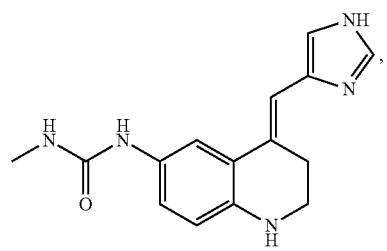
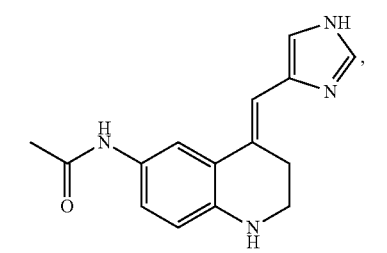
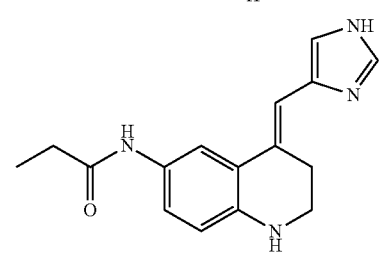
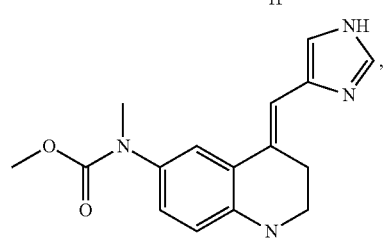
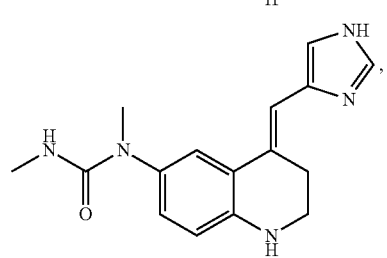
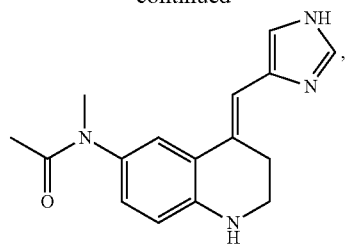
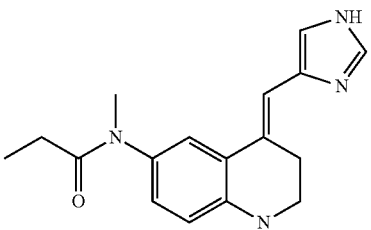
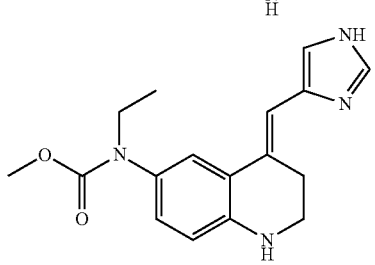
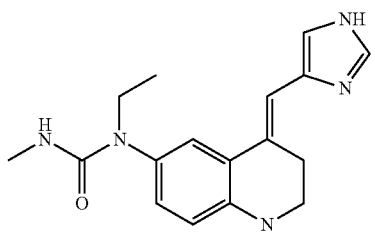
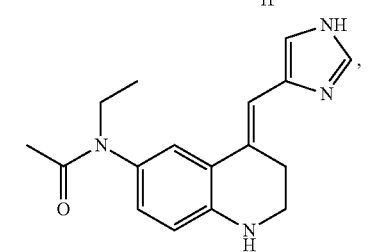
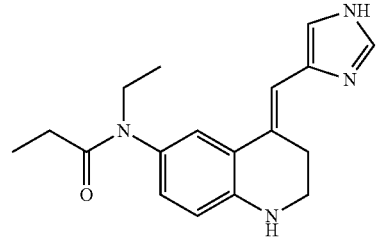
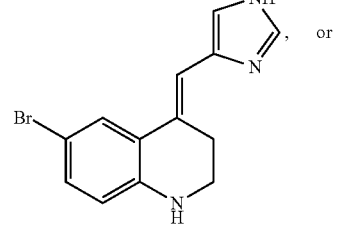, or

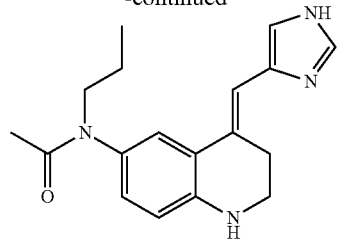
or the pharmaceutically acceptable prodrugs, salts, solvates or esters of each of these compounds.
4. The compound of claim 3 which is
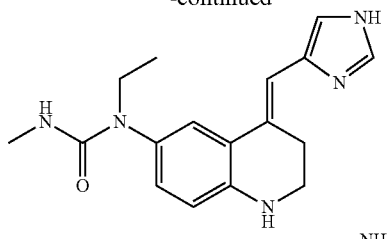
or a pharmaceutically acceptable prodrug, salt, solvate or ester thereof.
* * * * *